United States Patent [19]
Tryggvason et al.

[11] Patent Number: 6,143,505
[45] Date of Patent: *Nov. 7, 2000

[54] LAMININ CHAINS: DIAGNOSTIC AND THERAPEUTIC USE

[76] Inventors: Karl Tryggvason, Fyysikontic 8, FIN-90570, Oulu, Finland; Pekka Kallunki, 8722 La Jolla Dr., Unit 99, La Jolla, Calif. 92037; Charles Pyke, Solbakken 4, DK-3400, Hilleroo, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/800,593

[22] Filed: Feb. 18, 1997

Related U.S. Application Data

[62] Division of application No. 08/317,450, Oct. 4, 1994, Pat. No. 5,660,982.
[51] Int. Cl.[7] .................. G01N 33/53; G01N 33/574; G01N 33/566; C12N 5/06
[52] U.S. Cl. .................. 435/7.1; 435/7.23; 435/344.1; 435/960; 436/501; 436/813
[58] Field of Search ................... 435/7.1, 7.23, 435/344.1, 960; 436/501, 813

[56] References Cited

U.S. PATENT DOCUMENTS 5,152,980  10/1992  Strom et al. .

OTHER PUBLICATIONS

Embase Abstract No: 97163048, 1997.
Snyder et al., "λgt 11: Gene Isolation with Antibody Probes and Other Applications", in Methods in Enzymology vol. 154 pp 107–128, 1987.

Hao et al., "Differential Expression of Laminin 5 (α3β3γ2) by Human Malignant and Normal Prostate," Am. J. of Pathol., 149(4):1341–1349, 1996.

Matsui et al, "$\gamma^2$ Chain of Laminin −5 Is Recognized by Monoclonal Antibody GB3," J. Invest. Dermatol. 105(5):648–652, 1995.

Pyke et al., "The $\gamma^2$ Chain of Kalinin/Laminin 5 Is Preferentially Expressed in Invading Malignant Cells in Human Cancers," Am. J. Pathol. 145(4):782–791, Oct. 6, 1994.

Pyke et al. "Laminin −5 Is a Marker of Invading Cancer Cells in Some Human Carcinomas . . . ," Cancer Res. 55:4132–4139, 1995.

Verrando et al., "Nicein (BM600) in Junctional Epidermolysis Bullosa: Polyclonal Antibodies Provide New Clues for Pathogenic Role," J. Invest. Dermatol. 101(5):738–743, 1993.

Verrando et al., "Mononclonal Antibody GB3 Defines a Widespread Defect of Several Basement Membranes . . . ", Lab. Invest. 64(1):85–92, 1991.

Wewer et al., "Selective Assembly of Laminin Variants by Human Carcinoma Cells," 71(5): 719–730, Nov. 1994.

*Primary Examiner*—James C. Housel
*Assistant Examiner*—Ja-Na Hines
*Attorney, Agent, or Firm*—Fay, Sharpe, Fagan, Minnich, & McKee

[57] ABSTRACT

The instant invention provides for the identification, diagnosis, monitoring, and treatment of invasive cells using the laminin 5 gamma-2 chain protein or nucleic acid sequence, or antibodies thereto.

4 Claims, 7 Drawing Sheets

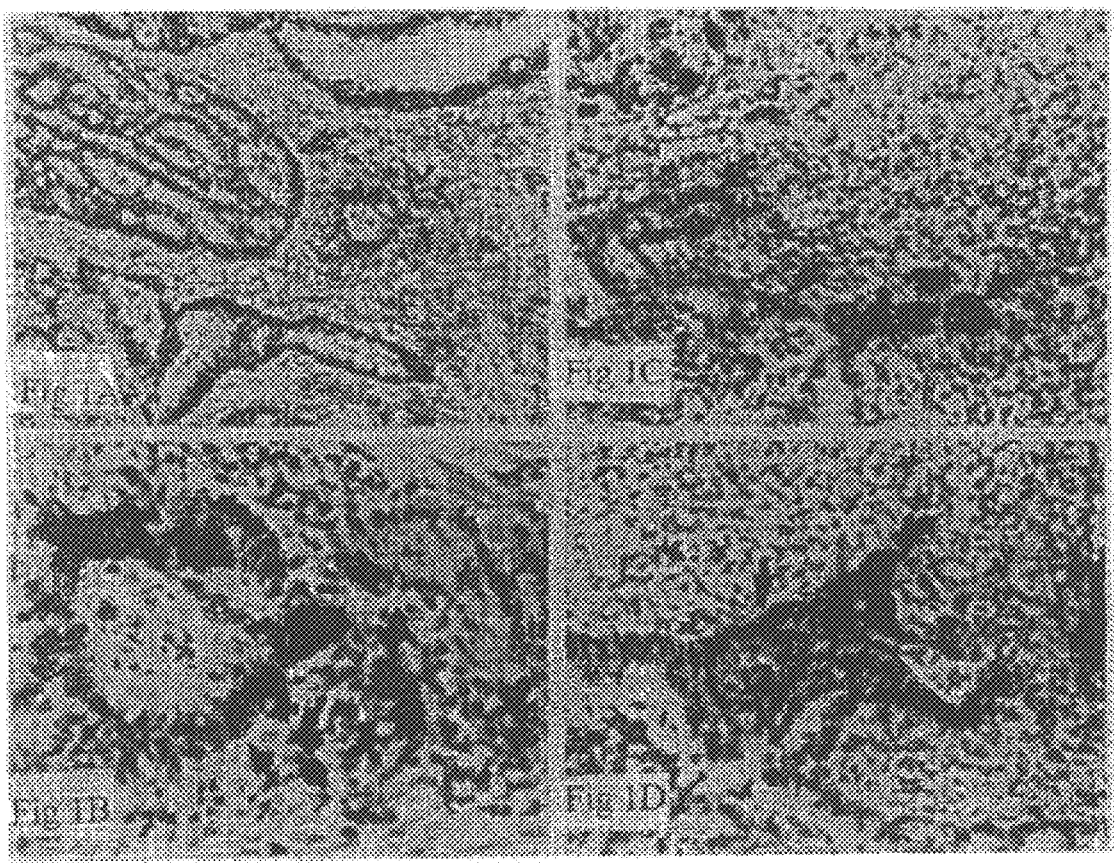

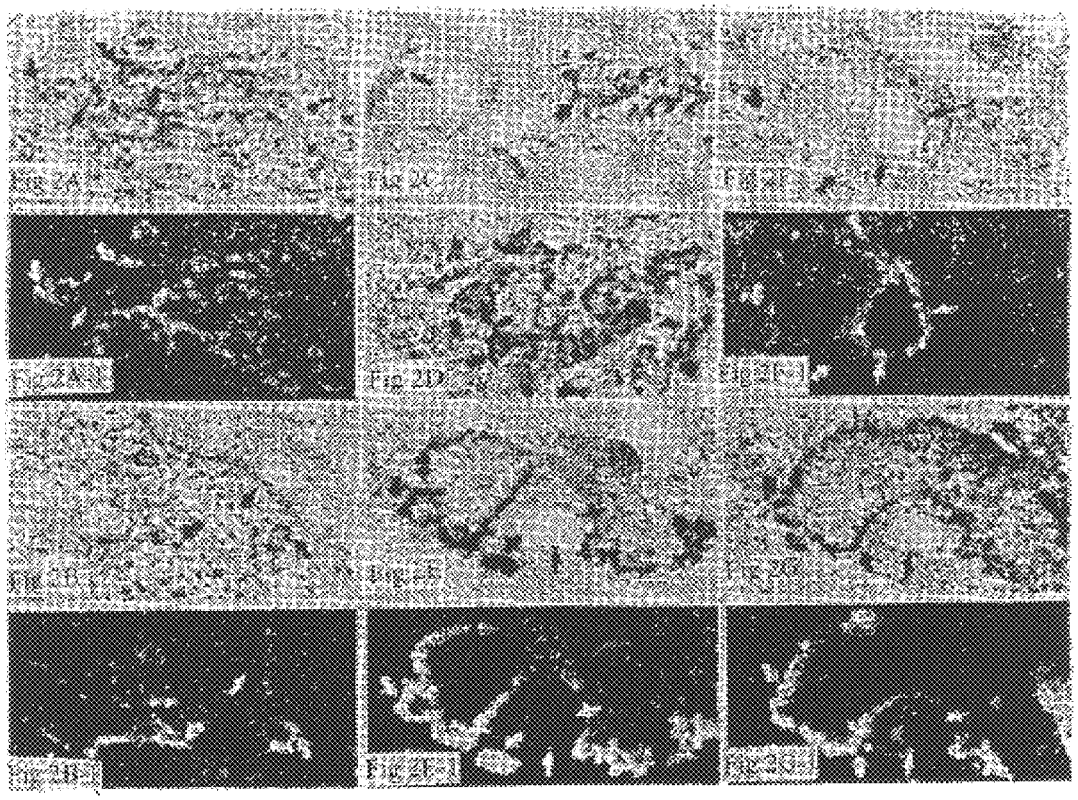

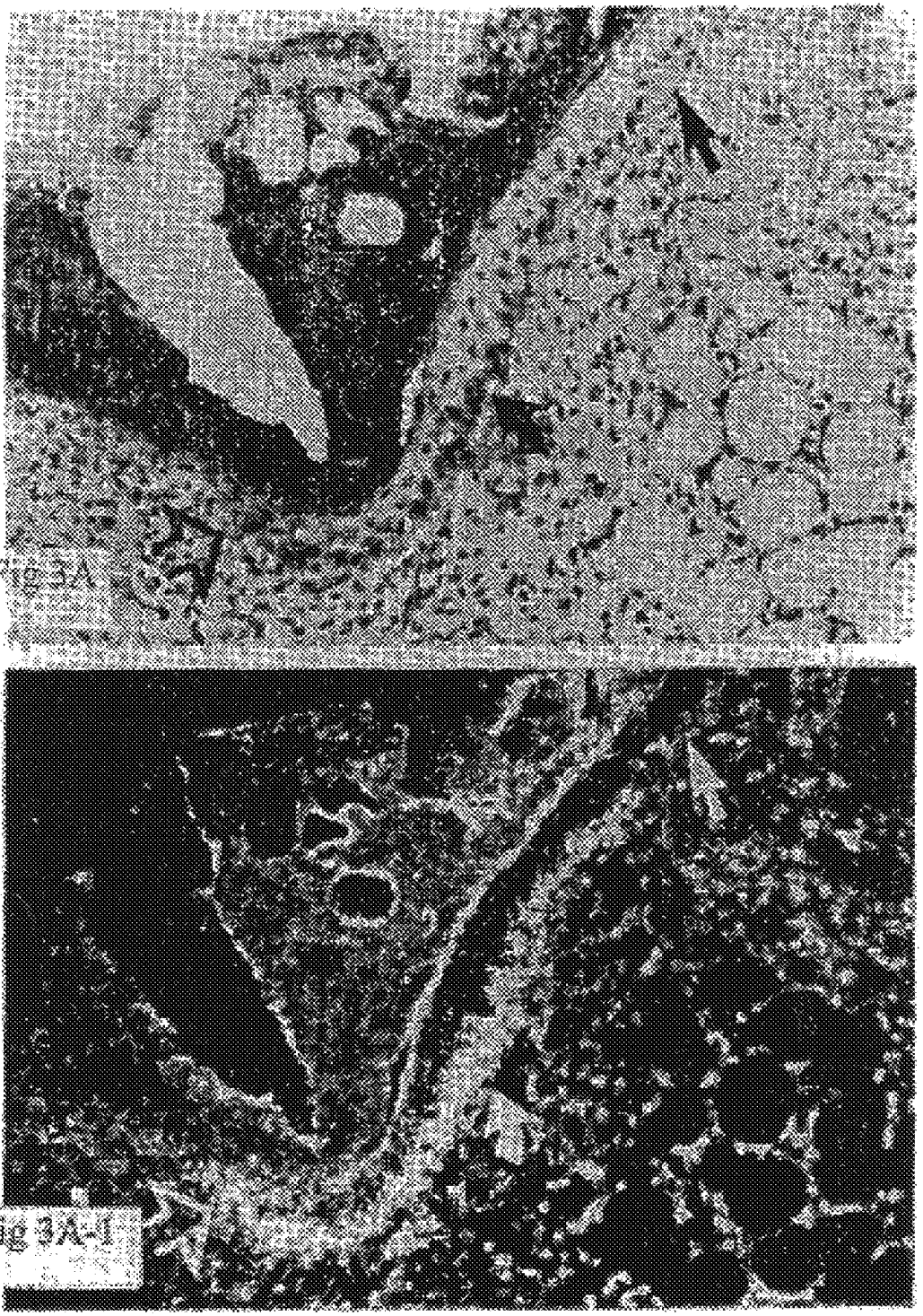

FIG 4A  (SEQ ID NO.:12 & 13)

```
   1 gaccacctga tcgaaggaaa aggaaggcac agcggagcgc agagtgagaa ccaccaaccg
  61 aggcgccggg cagcgacccc tgcagcggag acagagactg agcggcccgg caccgccatg
   1                                                                  M
 121 cctgcgctct ggctgggctg ctgcctctgc ttctcgctcc tcctgcccgc agcccgggcc
   2  P  A  L   W  L  G  C   C  L  C   F  S  L   L  L  P  A   A  R  A
 181 acctccagga gggaagtctg tgattgcaat gggaagtcca ggcagtgtat ctttgatcgg
  22  T  S  R   R  E  V  C   D  C  N   G  K  S   R  Q  C  I   F  D  R
                           ↳ Domain V
 241 gaacttcaca gacaaactgg taatggattc cgctgcctca actgcaatga caacactgat
  42  E  L  H   R  Q  T  G   N  G  F   R  C  L   N  C  N  D   N  T  D
 301 ggcattcact gcgagaagtg caagaatggc ttttaccggc acagagaaag ggaccgctgt
  62  G  I  H   C  E  K  C   K  N  G   F  Y  R   H  R  E  R   D  R  C
 361 ttgccctgca attgtaactc caaaggttct cttagtgctc gatgtgacaa ctctggacgg
  82  L  P  C   N  C  N  S   K  G  S   L  S  A   R  C  D  N   S  G  R
 421 tgcagctgta aaccaggtgt gacaggagcc agatgcgacc gatgtctgcc aggcttccac
 102  C  S  C   K  P  G  V   T  G  A   R  C  D   R  C  L  P   G  F  H
 481 atgctcacgg atgcggggtg cacccaagac cagagactgc tagactccaa gtgtgactgt
 122  M  L  T   D  A  G  C   T  Q  D   Q  R  L   L  D  S  K   C  D  C
 541 gacccagctg gcatcgcagg gccctgtgac gcgggccgct gtgtctgcaa gccagctgtt
 142  D  P  A   G  I  A  G   P  C  D   A  G  R   C  V  C  K   P  A  V
 601 actggagaac gctgtgatag gtgtcgatca ggttactata atctggatgg ggggaaccct
 162  T  G  E   R  C  D  R   C  R  S   G  Y  Y   N  L  D  G   N  P
 661 gagggctgta cccagtgttt ctgctatggg cattcagcca gctgccgcag ctctcagaa
 182  E  G  C   T  Q  C  F   C  Y  G   H  S  A   S  C  R  S   S  A  E
                                                       ↳ Domain IV
 721 tacagtgtcc ataagatcac ctctaccttt catcaagatg ttgatggctg gaaggctgtc
 202  Y  S  V   H  K  I  T   S  T  F   H  Q  D   V  D  G  W   K  A  V
 781 caacgaaatg ggtctcctgc aaagctccaa tggtcacagc gccatcaaga tgtgtttagc
 222  Q  R  N   G  S  P  A   K  L  Q   W  S  Q   R  H  Q  D   V  F  S
 841 tcagcccaac gactagatcc tgtctatttt gtggctcctg ccaaatttct tgggaatcaa
 242  S  A  Q   R  L  D  P   V  Y  F   V  A  P   A  K  F  L   G  N  Q
 901 caggtgagct atgggcaaag cctgtccttt gactaccgtg tggacagagg aggcagacac
 262  Q  V  S   Y  G  Q  S   L  S  F   D  Y  R   V  D  R  G   G  R  H
 961 ccatctgccc atgatgtgat cctggaaggt gctggtctac ggatcacagc tcccttgatg
 282  P  S  A   H  D  V  I   L  E  G   A  G  L   R  I  T  A   P  L  M
1021 ccacttggca agacactgcc ttgtgggctc accaagactt acacattcag gttaaatgag
 302  P  L  G   K  T  L  P   C  G  L   T  K  T   Y  T  F  R   L  N  E
1081 catccaagca ataattggag cccccagctg agttactttg agtatcgaag gttactgcgg
 322  H  P  S   N  N  W  S   P  Q  L   S  Y  F   E  Y  R  R   L  L  R
1141 aatctcacag ccctccgcat ccgagctaca tatggagaat acagtactgg gtacattgac
 342  N  L  T   A  L  R  I   R  A  T   Y  G  E   Y  S  T  G   Y  I  D
1201 aatgtgaccc tgatttcagc ccgccctgtc tctggagccc cagcaccctg ggttgaacag
 362  N  V  T   L  I  S  A   R  P  V   S  G  A   P  A  P  W   V  E  Q
1261 tgtatatgtc ctgttgggta caagggcaa ttctgccagg attgtgcttc tggctacaag
 382  C  I  C   P  V  G  Y   K  G  Q   F  C  Q   D  C  A  S   G  Y  K
        ↳ Domain III
1321 agagattcag cgagactggg gccttttggc acctgtattc cttgtaactg tcaaggggga
 402  R  D  S   A  R  L  G   P  F  G   T  C  I   P  C  N  C   Q  G  G
1381 ggggcctgtg atccagacac aggagattgt tattcagggg atgagaatcc tgacattgag
 422  G  A  C   D  P  D  T   G  D  C   Y  S  G   D  E  N  P   D  I  E
1441 tgtgctgact gcccaattgg tttctacaac gatccgcacg accccgcag ctgcaagcca
 442  C  A  D   C  P  I  G   F  Y  N   D  P  H   D  P  R  S   C  K  P
1501 tgtccctgtc ataacgggtt cagctgctca gtgattccgg agacggagga ggtggtgtgc
 462  C  P  C   H  N  G  F   S  C  S   V  I  P   E  T  E  E   V  V  C
```

FIG 4B

(SEQ ID NO.:12 & 13)

```
1561 aataactgcc ctcccgggt caccggtgcc cgctgtgagc tctgtgctga tggctacttt
 482  N  N  C    P  P  G  V    T  G  A    R  C  E    L  C  A  D    G  Y  F
1621 ggggacccct ttggtgaaca tggcccagtg aggccttgtc agccctgtca atgcaacagc
 502  G  D  P    F  G  E  H    G  P  V    R  P  C    Q  P  C  Q    C  N  S
1681 aatgtggacc ccagtgcctc tgggaattgt gaccggctga caggcaggtg tttgaagtgt
 522  N  V  D    P  S  A  S    G  N  C    D  R  L    T  G  R  C    L  K  C
1741 atccacaaca cagccggcat ctactgcgac cagtgcaaag caggctactt cggggaccca
 542  I  H  N    T  A  G  I    Y  C  D    Q  C  K    A  G  Y  F    G  D  P
1801 ttggctccca acccagcaga caagtgtcga gcttgcaact gtaaccccat gggctcagag
 562  L  A  P    N  P  A  D    K  C  R    A  C  N    C  N  P  M    G  S  E
1861 cctgtaggat gtcgaagtga tggcacctgt gtttgcaagc caggatttgg tggccccaac
 582  P  V  G    C  R  S  D    G  T  C    V  C  K    P  G  F  G    G  P  N
1921 tgtgagcatg gagcattcag ctgtccagct tgctataatc aagtgaagat tcagatggat
 602  C  E  H    G  A  F  S    C  P  A    C  Y  N    Q  V  K  I    Q  M  D
                              ↳ Domain I/II
1981 cagtttatgc agcagcttca gagaatggag ccctgattt caaaggctca gggtggtgat
 622  Q  F  M    Q  Q  L  Q    R  M  E    A  L  I    S  K  A  Q    G  G  D
2041 ggagtagtac ctgatacaga gctggaaggc aggatgcagc aggctgagca ggcccttcag
 642  G  V  V    P  D  T  E    L  E  G    R  M  Q    Q  A  E  Q    A  L  Q
2101 gacattctga gagatgccca gatttcagaa ggtgctagca gatcccttgg tctccagttg
 662  D  I  L    R  D  A  Q    I  S  E    G  A  S    R  S  L  G    L  Q  L
2161 gccaaggtga ggagccaaga aacagctac cagagccgcc tggatgacct caagatgact
 682  A  K  V    R  S  Q  E    N  S  Y    Q  S  R    L  D  D  L    K  M  T
2221 gtggaaagag ttcgggctct gggaagtcag taccagaacc gagttcggga tactcacagg
 702  V  E  R    V  R  A  L    G  S  Q    Y  Q  N    R  V  R  D    T  H  R
2281 ctcatcactc agatgcagct gagcctggca gaaagtgaag cttccttggg aaacactaac
 722  L  I  T    Q  M  Q  L    S  L  A    E  S  E    A  S  L  G    N  T  N
2341 attcctgcct cagaccacta cgtggggcca aatggcttta aaagtctggc tcaggaggcc
 742  I  P  A    S  D  H  Y    V  G  P    N  G  F    K  S  L  A    Q  E  A
2401 acaagattag cagaaagcca cgttgagtca gccagtaaca tggagcaact gacaagggaa
 762  T  R  L    A  E  S  H    V  E  S    A  S  N    M  E  Q  L    T  R  E
2461 actgaggact attccaaaca agccctctca ctggtgcgca aggccctgca tgaaggagtc
 782  T  E  D    Y  S  K  Q    A  L  S    L  V  R    K  A  L  H    E  G  V
2521 ggaagcggaa gcggtagccc ggacggtgct gtggtgcaag ggcttgtgga aaaattggag
 802  G  S  G    S  G  S  P    D  G  A    V  V  Q    G  L  V  E    K  L  E
2581 aaaaccaagt ccctggccca gcagttgaca agggaggcca ctcaagcgga aattgaagca
 822  K  T  K    S  L  A  Q    Q  L  T    R  E  A    T  Q  A  E    I  E  A
2641 gataggtctt atcagcacag tctccgcctc ctggattcag tgtctccgct tcagggagtc
 842  D  R  S    Y  Q  H  S    L  R  L    L  D  S    V  S  P  L    Q  G  V
2701 agtgatcagt cctttcaggt ggaagaagca aagaggatca acaaaaagc ggattcactc
 862  S  D  Q    S  F  Q  V    E  E  A    K  R  I    K  Q  K  A    D  S  L
2761 tcaagcctgg taaccaggca tatggatgag ttcaagcgta cacaaaagaa tctgggaaac
 882  S  S  L    V  T  R  H    M  D  E    F  K  R    T  Q  K  N    L  G  N
2821 tggaaagaag aagcacagca gctcttacag aatggaaaaa gtgggagaga gaaatcagat
 902  W  K  E    E  A  Q  Q    L  L  Q    N  G  K    S  G  R  E    K  S  D
2881 cagctgcttt cccgtgccaa tcttgctaaa agcagagcac aagaagcact gagtatggc
 922  Q  L  L    S  R  A  N    L  A  K    S  R  A    Q  E  A  L    S  M  G
2941 aatgccactt tttatgaagt tgagagcatc cttaaaaacc tcagagagtt tgacctgcag
 942  N  A  T    F  Y  E  V    E  S  I    L  K  N    L  R  E  F    D  L  Q
3001 gtggacaaca gaaaagcaga agctgaagaa gccatgaaga gactctccta catcagccag
 962  V  D  N    R  K  A  E    A  E  E    A  M  K    R  L  S  Y    I  S  Q
3061 aaggtttcag atgccagtga caagacccag caagcagaaa gagccctggg gagcgctgct
 982  K  V  S    D  A  S  D    K  T  Q    Q  A  E    R  A  L  G    S  A  A
3121 gctgatgcac agagggcaaa gaatggggcc ggggaggccc tggaaatctc cagtgagatt
1002  A  D  A    Q  R  A  K    N  G  A    G  E  A    L  E  I  S    S  E  I
```

FIG 4C (SEQ ID NO.:12 & 13)

```
3181 gaacaggaga ttgggagtct gaacttggaa gccaatgtga cagcagatgg agccttggcc
1022  E  Q  E    I  G  S  L   N  L  E    A  N  V    T  A  D  G    A  L  A
3241 atggaaaagg gactggcctc tctgaagagt gagatgaggg aagtggaagg agagctggaa
1042  M  E  K    G  L  A  S   L  K  S    E  M  R    E  V  G    E  L  E
3301 aggaaggagc tggagtttga cacgaatatg gatgcagtac agatggtgat tacagaagcc
1062  R  K  E    L  E  F  D   T  N  M    D  A  V    Q  M  V  I   T  E  A
3361 cagaaggttg ataccagagc caagaacgct ggggttacaa tccaagacac actcaacaca
1082  Q  K  V    D  T  R  A   K  N  A    G  V  T    I  Q  D  T   L  N  T
3421 ttagacggcc tcctgcatct gatggaccag cctctcagtg tagatgaaga ggggctggtc
1102  L  D  G    L  L  H  L   M  D  Q    P  L  S    V  D  E  E   G  L  V
3481 ttactggagc agaagctttc ccgagccaag acccagatca acagccaact gcggcccatg
1122  L  L  E    Q  K  L  S   R  A  K    T  Q  I    N  S  Q  L   R  P  M
3541 atgtcagagc tggaagagag ggcacgtcag cagaggggcc acctccattt gctggagaca
1142  M  S  E    L  E  E  R   A  R  Q    Q  R  G    H  L  H  L   L  E  T
3601 agcatagatg ggattctggc tgatgtgaag aacttggaga acattaggga caacctgccc
1162  S  I  D    G  I  L  A   D  V  K    N  L  E    N  I  R  D   N  L  P
3661 ccaggctgct acaataccca ggctcttgag caacagtgaa gctgccataa atatttctca
1182  P  G  C    Y  N  T  Q   A  L  E    Q  Q  *

3721 actgaggttc ttgggataca gatctcaggg ctcgggagcc atgtcatgtg agtgggtggg
3781 atggggacat ttgaacatgt ttaatgggta tgctcaggtc aactgacctg accccattcc
3841 tgatcccatg gccaggtggt tgtcttattg caccatactc cttgttcct gatgctgggc
3901 atgaggcaga taggcactgg tgtgagaatg atcaaggatc tggaccccaa agatagactg
3961 gatggaaaga caaactgcac aggcagatgt ttgcctcata atagtcgtaa gtggagtcct
4021 ggaatttgga caagtgctgt tgggatatag tcaacttatt ctttgagtaa tgtgactaaa
4081 ggaaaaaact ttgactttgc ccaggcatga aattcttcct aatgtcagaa cagagtgcaa
4141 cccagtcaca ctgtggccag taaaatacta ttgcctcata ttgtcctctg caagcttctt
4201 gctgatcgaa gttcctccta cttacaaccc agggtgtgaa catgttctcc attttcaagc
4261 tggaagaagt gagcagtgtt ggagtggagga cctgtaaggc aggcccattc agagctatgg
4321 tgcttgctgg tgcctgccac cttcaagttc tggacctggg catgacatcc tttctttaa
4381 tgatgccatg gcaacttaga gattgcattt ttattaaagc atttcctacc agcaaagcaa
4441 atgttgggaa agtatttact ttttcggttt caaagtgata gaaaagtgtg gcttgggcat
4501 tgaaagaggt aaaattctct agatttatta gtcctaattc aatcctactt ttcgaacacc
4561 aaaaatgatg cgcatcaatg tattttatct tattttctca atctcctctc tctttcctcc
4621 acccataata agagaatgtt cctactcaca cttcagctgg gtcacatcca tccctccatt
4681 catccttcca tccatctttc catccattac ctccatccat ccttccaaca tatatttatt
4741 gagtacctac tgtgtgccag gggctggtgg gacagtggtg acatagtctc tgccctcata
4801 gagttgattg tctagtgagg aagacaagca ttttaaaaaa ataaatttaa acttacaaac
4861 tttgtttgtc acaagtggtg tttattgcaa taaccgcttg gtttgcaacc tctttgctca
4921 acagaacata tgttcaagaa ccctcccatg ggcactgagt ttggcaagga tgacagagct
4981 ctgggttgtg cacatttctt tgcattccag cgtcactctg tgccttctac aactgattgc
5041 aacagactgt tgagttatga taacaccagt gggaattgct ggaggaacca gaggcacttc
5101 cacttggct gggaagacta tggtgctgcc ttgcttctgt atttccttgg attttcctga
5161 aagtgttttt aaataaagaa caattgttag atgccaaaaa  //
```

FIG 4D
(SEQ ID NO.:14 & 15)
```
3421 ttagacggcc tcctgcatct gatgggtatg tgaacccaca acccacaacc ttccagctcc
1102  L   D   G    L   L   H   L    M   G   M    *

3481 atgctccagg gctttgctcc agaacactca ctatacctag ccccagcaaa ggggagtctc
3541 agctttcctt aaggatatca gtaaatgtgc tttgtttcca ggcccagata actttcggca
3601 ggttcccta catttactgg accctgtttt accgttgcta agatgggtca ctgaacacct
3661 attgcacttg ggggtaaagg tctgtgggcc aaagaacagg tgtatataag caacttcaca
3721 gaacacgaga cagcttggga atcctgctaa agagtctggc ctggaccctg agaagccagt
3781 ggacagtttt aagcagagga ataacatcac cactgtatat ttcagaaaga tcactagggc
3841 agccgagtgg aggaaagctt gaagaggggg ttagagagaa ggcaggttga gactacttaa
3901 gatattgttg aaataattga agagagaaat gacaggagcc tgctctaagg cagtagaatg
3961 gtggctggga agatgtgaag gaagattttc ccagtctgtg aagtcaagaa tcacttgccg
4021 gccggtgtg gtggctcacg cctgtaattc tagcactttg ggagactgaa gcgggtggat
4081 cacccgaggt caggagttga agaccagcct ggccaacatg gtgaaaccct gtctctacta
4141 aaagtacaaa aattagctgg atgatggtgg tgggcgcctg taattccagc tactcaggag
4201 tctgaggcag gagaatcgct tgaacccagg aggcgaggtt acagtgagcc aagattgcac
4261 cactgctctt ccagcctggg aacagagaga ctgcctaaaa aaaaaaaaa aaaaaa //
```

LAMININ CHAINS: DIAGNOSTIC AND THERAPEUTIC USE

This is a divisional of application Ser. No. 08/317,450, filed Oct. 4, 1994, now U.S. Pat. No. 5,660,982.

BACKGROUND OF THE INVENTION

Laminins are a family of basement membrane proteins which function in cell differentiation, adhesion, and migration, in addition to being true structural components (Tryggvason K, *Curr. Opn. Cell Biol.*, 1993, 5:877–882, this and all following references are hereby incorporated by reference). The laminin molecule is a cross-shaped heterotrimer consisting of one heavy α chain (~400 kd) and two light chains, β and γ(130–200 kd) (nomenclature according to Burgeson et al., *Matrix Biol.*, 1994, 14:209–211). Laminin exists in numerous isoforms that are formed by different combinations of laminin chain varients which currently amount to at least nine.

Kalinin/laminin 5 (most likely also identical to the adhesion molecule nicein) is a recently identified laminin isoform which is a functional adhesion component for epithelial cells (Tryggvason, 1993, supra.; Burgeson et al., 1994, supra.; Rousselle et al., *J. Cell Bio.*, 1991, 114:567–576; Kallunki et al., *J. Cell Biol.*, 1992, 119:679–693; Marinkovich et al., *J. Biol. Chem.*, 1992, 267:17900–17906; Vailly et al., *Eur. J. Biochem.*, 1994, 219:209–218). Kalinin/laminin 5 contains unique laminin varient chains, one of which, the γ2 chain, has recently been cloned and sequenced (Kallunki et al., 1992, supra., previously named B2t). The γ2 chain has a mass of ~130 kd and is thus smaller than the "classical"~200 kd β1 and γ1 light chains of laminin. The domain structure of the γ2 chain also differs from that of the γ1 chain in that it lacks the amino-terminal globular domain (domain VI) believed to function in intermolecular cross-linking of laminin molecules to form networks (Yurcheno and O'Rear, in *Molecular and Cellular Aspects of Basement Membranes*, 1993, (ed. Rohrbach and Timpl, Academic Press, San Diego, pp. 20–47). In addition, domains III, IV, and V (containing EGF-like repeats) in γ2 are shorter than in the γ1 chain (Kallunki et al., 1992, supra.).

By in situ hybridization the γ2 chain was found to be expressed in epithelial cells of many embryonic tissues such as those of skin, lung, and kidney (Kallunki et al., 1992, supra.), and antibodies to kalinin/laminin 5, react with basement membranes of the same tissues (Rousselle et al., 1991, supra.; Verrando et al., *Lab. Invest.*, 1991, 64:85–92).

The different laminin chains have been shown to have quite varying tissue distribution as determined by immunohistological studies, Northern, and in situ hybridization analyses. For example, the A and M chains on the one hand, and the B 1 (β1) and S (β2) chains on the other, have been shown to be mutually exclusive (see for example Vuolteenaho et al., *J. Cell Biol.*, 1994, 124:381–394). In vitro studies have indicated that laminin mediates a variety of biological functions such as stimulation of cell proliferation, cell adhesion, differentiation, and neurite outgrowth. The cellular activities are thought to be mediated by cell membrane receptors, many of which are members of the integrin family (Ruoslahti, E. *J. Clin. Invest.*, 1991, 87:1–5; Mecham, R. P. *FASEB J.*, 1991, 5:2538–2546; Hynes, R. *Cell*, 1992, 69:11–25).

Recently a new nomenclature for describing laminins has been agreed to as in the following Table 1 (after Burgeson et al., 1994, supra.)

TABLE 1

| laminin chains and genes | | | heterotrimers of laminin | | |
|---|---|---|---|---|---|
| New | Previous | Gene | New | Chains | Previous |
| α1 | A, Ae | LAMA1 | laminin-1 | α1β1γ1 | EHS laminin |
| α2 | M, Am | LAMA2 | laminin-2 | α2β1γ1 | merosin |
| α3 | 200 kDa | LAMA3 | laminin-3 | α1β2γ1 | s-laminin |
| β1 | B1, B1e | LAMB1 | laminin-4 | α2β2γ1 | s-merosin |
| β2 | S, B1s | LAMB2 | laminin-5 | α3β3γ2 | kalinin/nicein |
| β3 | 140 kDa | LAMB3 | laminin-6 | α3β1γ1 | k-laminin |
| γ1 | B2, B2e | LAMC1 | laminin-7 | α3β2γ1 | ks-laminin |
| γ2 | B2t | LAMC2 | | | |

SUMMARY OF THE INVENTION

The instant invention provides for methods of detecting kalinin/laminin 5 expression in tissue comprising detecting a signal from assayed tissue, such signal resulting from specifically hybridizing tissue with an effective amount of a nucleic acid probe, which probe contains a sense or antisense portion of kalinin/laminin 5 gamma-2 nucleic acid sequence (Kallunki et al., 1992, supra.). In particular, where the nucleic acid probe is DNA, RNA, radiolabelled, enzyme labelled, chemiluminescent labelled, avidin or biotin labelled, derived from human kalinin/laminin 5 gamma-2 nucleic acid sequence, incorporated into an extrachromasomal self-replicating vector, a viral vector, is linear, circularized, or contains modified nucleotides. In the preferred embodiment the probes are linearized specific regions of the γ2 gene.

The instant invention also provides for methods for detecting the presence of invasive cells in tissue comprising detecting a signal from assayed tissue, such signal resulting from contacting tissue with an effective amount of a nucleic acid probe, which probe contains a sense or antisense portion of kalinin/laminin 5 gamma-2 nucleic acid sequence (Kallunki et al., 1992, supra.). In particular, where the nucleic acid probe is DNA, RNA, radiolabelled, enzyme labelled, chemiluminescent labelled, avidin or biotin labelled, derived from human kalinin/laminin 5 gamma-2 nucleic acid sequence, incorporated into an extrachromasomal self-replicating vector, a viral vector, is linear, circularized, or contains modified nucleotides. In the preferred embodiment the probes are linearized specific regions of the γ2 gene. The instant method also provides for the diagnosis of the absence of γ2 chain expression, useful for the monitoring of therapies, and the progress of malignant cell transformation leading to accurate determination of the extent of invasive cell activity.

The instant invention further provides for a method for detecting kalinin/laminin 5 expression in tissue comprising detecting a signal from assayed tissue, such signal resulting from contacting tissue with an effective amount of a labeled probe, which probe contains an antibody immunoreactive with a portion of kalinin/laminin 5 gamma-2 protein.

Further provided is a method for detecting invasive cells in tissue comprising detecting a signal from assayed tissue, such signal resulting from contacting tissue with an effective amount of a labeled probe, which probe contains an antibody immunoreactive with a portion of kalinin/laminin 5 gamma-2 protein. Also provided is a method for detecting kalinin/laminin 5 in tissue comprising detecting a signal from assayed tissue, such signal resulting from contacting tissue with an effective amount of a labeled probe, which probe contains an antibody immunoreactive with a portion of kalinin/laminin 5 gamma-2 protein. Thus the method of the instant invention provides for the absence of such signal as diagnostic for the absence of invasive cells.

BRIEF DESCRIPTION OF THE DRAWINGS

FIG. 1 shows In situ hybridization of a specimen of colon adenocarcinoma for γ2 chain mRNA using a S-35 labeled anti-sense RNA probe derived from plasmid pbb2r-02. Magnification:1A×100; 1B–1D×640.

FIG. 2 shows In situ hybridization for γ2 chain mRNA on sections of ductal mammary carcinoma (2A), malignant melanoma (2B), squamous cell carcinoma of the skin (2C–2D), and squamous cell carcinoma of the vulva (2E–2G). Magnification: 2C×100, all others×640.

FIG. 3 is incisionally wounded mouse skin (72 hours after wounding) showing signal for γ2 chain in keratinocytes at the leading edge of the migrating epithelium (curved arrow). Magnification:×640.

FIG. 4 shows the nucleic acid sequence for the γ2 chain cDNA and the derived amino acid sequence. FIG. 4A is the full cDNA for the 5,200 base pair sequence, available from EMB/GenBank/DDBJ under the accession number Z15008. FIG. 4B is the nucleotide and derived amino acid sequence of the alternative 3' end sequence from cDNA clones providing a sequence of 4,316 base pairs, available from EMB/GenBank/DDBJ under the accession number Z15009. (Kallunki et al., 1992, supra.).

DETAILED DESCRIPTION OF THE INVENTION

Epidermolysis bullosa (EB) is a group of mechano-bullous disorders characterized by fragility of the skin and mucous membranes (see Lin & Carter eds., Epidermolysis bullosa, Basic and clinical aspects, 1992, Springer Verlag, N.Y.; Fine et al., J. Am. Acad. Dermatol., 1991, 24:119–135). The junctional forms of EB (JEB) are characterized by tissue separation at the level of the lamina lucida within the dermal-epidermal basement membrane, and no specific mutation had yet to be reported. Recently it has been proposed that the genes for a lamina lucida protein kalinin/nicein/epiligin may be a candidate in some forms of JEB (Verrando et al., 1991, supra.). Several lines of evidence suggest that anchoring filament proteins could be defective in some forms of JEB. First, attenuation or absence of immunoreactivity with anti-kalinin(epiligrin) antibodies has been noted in the skin of patients with the most severe (Herlitz) type of JEB. The immunofluorescence staining patterns may be of prognostic value in classifying JEB, and these immunoreagents have been used for prenatal diagnosis of JEB using fetal skin biopsy specimins. Second, the kalinin/laminin 5 γ2 chain is expressed in epithelial cells of the skin, trachea and kidneys, tissues which are frequently affected by JEB.

Since the majority of cases are of the generalized (Herlitz) phenotype (H-JEB), JEB patients have been classified into Herlitz and non-Herlitz types. Clinical features of H-JEB include mechanical fragility of the skin, with widespread blistering and erosions, rapid deterioration and neonatal death, often from sepsis. Longterm survival is rare.

Efforts to identify the basic defect in JEB began with the observation that a monoclonal antibody that binds to the lamina lucida of the epidermal basement membrane zone of normal skin, fails to react with the lamina lucida of H-JEB skin (Verrando et al., 1991, supra.). The antigen recognized by this antibody was purified from keratinocyte culture medium and termed BM600/nicein. Keratinocytes cultured from the skin of H-JEB patients attach poorly to substrate and fail to accumulate immunologically detectable nicein. Further experiments with antibodies specific for the α3 chain of nicein, demonstrated that they were capable of inducing the rounding and detachment of adherent keratinocytes without affecting fibroblasts (Rousselle et al., 1991, supra.). Thus the correlation in vivo and in vitro of the dermoepidermal separation with deficient nicein/kalinin/laminin 5 immunoreactivity and the separation induced by anti-nicein antibody have made the genes encoding this protein strong candidates for the site of H-JEB mutations.

The importance of the γ2 chain of nicein/kalinin/laminin 5 in JEB, and epithelial tissues prompted the investigation into the role such adhesion contacts between epithelial cells may play in abberant cells. Of primary interest was the role γ2 chain of nicein/kalinin/laminin 5 abberant expression may play in cancer tissue, and a possible role in cancer dissemination.

It has been recently shown that in colon adenocarcinoma, a significant positive correlation between the degree of tumor budding and the recurrence of tumors following curative surgery exists, and that this fact is likely to reflect a higher invasive potential of budding cancer cells as compared with cancer cells located deeper in the tumor (Hase et al., Dis. Colon Rectum, 1993, 36:627–635). Therefore, as demonstrated in Example 3 below, the instant invention allows for the useful prognostic determination of success of surgery, means for monitoring progression of tumor budding and subsequent prognosis.

The identification of the role of γ2 chain allows for the novel use of kalinin/laminin 5 γ2 chain and its ligand, as diagnostic probes of the tumor cell/basement membrane adhesion interface that is crucial for the invasion of non-malignant tissues, and identifies invasive cells.

Thus the identification of the role of γ2 chain allows for the novel therapeutic intervention of binding of kalinin/laminin 5 to its ligand, and thereby reducing the tumor cell/basement membrane adhesion that is crucial for the invasion of non-malignant tissues, and method for inhibiting the budding of tumor masses, and a means for determining the level of γ2 chain expression as a measure of budding activity of a given tumor.

As demonstrated in Example 3 below, the γ2 chain of kalinin/laminin 5 is preferentially expressed by invasively growing malignant cells in human carcinomas. Furthermore, migrating keratinocytes in wound healing also expressed this gene, pointing to a role of γ2 chain in epithelial cell migration both in malignant and in nonmalignant pathological conditions. The consistent expression of the γ2 chain gene in invading cancer cells reflects a functional importance of this molecule in vivo in establishing contacts between the invading malignant cells and a provisional matrix in the immediate surroundings of the cancer cells. The instant invention provides methods for the identification of, and diagnosis of invasive cells and tissues, and for the monitoring of the progress of therapeutic treatments.

In a preferred embodiment of this aspect of the instant invention the nucleic acid probe comprise a specifically hybridizing fragment of the γ2 chain cDNA nucleic acid sequence. In this embodiment, the nucleic acid sequence comprises all or a specifically hybridizing fragment of an open reading frame of the nucleic acid sequence for the γ2 chain (FIG. 4) encoding the amino acid sequence of the γ2 chain (FIG. 4). It will be understood that the term "specifically hybridizing" when used to describe a fragment of nucleic acid encoding a human laminin γ2 chain gene is intended to mean that, nucleic acid hybridization of such a fragment is stable under high stringency conditions of hybridization and washing as the term "high stringency" would be understood by those having skill in the molecular biological arts.

Further, the instant invention provides for the therapeutic treatment of such invasive tissues by using γ2 chain or biologically active fragments thereof to interfere with the interactions between aberrant γ2 chain and surrounding tissues. The instant invention also provides for the intervention of γ2 chain interaction with surrounding tissues by using specific anti-γ2 chain antibodies (monoclonal or polyclonal) to inhibit the γ2 chain biological activity.

The instant disclosure also allows one to ablate the invasive cell phenotypic γ2 chain expression by using genetic manipulation to "knock-out" the functional expression of the γ2 chain gene in cancer cells, or to completely "knock-out" the functional γ2 chain gene in the genome of cancer cells. Such knock-outs can be accomplished by using genetic molecular biological techniques for inserting homologous recombination into genomic DNA, targeted transposon insertion, or random insertion/deletion mutations in the genomic DNA.

The instant disclosure also allows for the therapeutic treatment of invasive cell phenotype by the inhibition of functional γ2 chain expression in targeted cells by using anti-sense technology, such methods for anti-sense production, stabilization, delivery, and therapeutic approaches are reviewed in Uhlmann et al., 1990, *Chem. Reviews* 90:543–584).

Thus the instant invention provides for a method of detection, diagnosis, prognosis, monitoring, and therapeutic treatment of invasive cell phenotypes.

The examples below are meant by way of illustration, and are not meant to be limiting as to the scope of the instant disclosure.

EXAMPLE 1

Mutation in the γ2 Chain Gene LAMC2 is Critical in Some Cases of JEB

A unique scanning strategy using RT-PCR amplification of LAMC2 sequences was devised to detect truncated forms of γ2 chain gene transcripts (Pulkkinen et al., *Nature Genetics*, 1994, 6:293–298). The 3.6 kilobase coding sequence of the LAMC2 mRNA, was reverse transcribed and amplified with eight pairs of primers, producing overlapping PCR amplimers designated A–H. The PCR products were then examined by agarose gel electrophoresis, followed by MDE heteroduplex analysis. If bands with altered mobility were detected, the PCR products were sequenced, and compared with normal sequences from unaffected family members or unrelated individuals. Intron/exon borders were identified by PCR analysis of genomic DNA, deduced by comparison with cDNA sequences.

A Point Mutation Produces Exon Skipping

When a panel of five unrelated JEB patients were analysed, the primers used to amplify segment C (nt 1046–1537) produced markedly shortened band of 273 base pairs, as compared with the normal 491 base pairs. No evidence of the normal sized band was noted, suggesting that the patient was homozygous for this allele. Direct sequencing revealed that the shortened product resulted from the deletion of 219 base pairs corresponding to nucleotides 1184–1402 in the cDNA, thus exon 9 was deleted. The remaining nucleotide sequences within this and other PCR products did not reveal any additional mutations upon MDE analysis.

Subsequent examination of the genomic DNA revealed that the sequences for exons 8, 9 and 10 were present, however a homozygous G for A substitution at the 3' acceptor splice site at the junction of intron 8 and exon 9, abolished the obligatory splice site sequence (AG).

Examination of another patient revealed that PCR product F (nt 2248–2777) corresponding to domains I and II of the γ2 chain, was a band with altered mobility. Sequencing the abnormal product revealed a 20 bp deletion, followed by a single base pair (G) insertion in the coding region corresponding to exon 16. This mutation causes a frameshift which results in a premature stop codon 51 base pairs downstream from the deletion-insertion, predicting a truncated kalinin/laminin 5 γ2 chain terminating at residue 830.

RT-PCR and MDE Analyses

RNA isolated from fibroblast cell cultures of JEB patients was used as template for RT-PCR of the LAMC2 mRNA. (Epidermal keratinocytes can also be used). cDNA was prepared from 50 μg of total RNA in a volume of 100 μL according to manufacturer's recommendations (BRL), and oligonucleotide primers were synthesized on the basis of the cDNA sequence (FIG. 4; Kallunki et al., 1992, supra.), to generate ~500 base pair products, which spanned the entire coding region.

For PCR amplification, 1 μL of cDNA was used as template and amplification conditions were 94 C. for 5 min followed by 95 C. for 45 sec, 60 C. for 45 sec and 72 C. for 45 sec for 35 cycles in an OmniGene thermal cycler (Marsh Scientific). Amplification was performed in a total volume of 25 μL containing 1.5 mM $MgCl_2$, and 2 U Taq polymerase (Boehringer Mannheim). Aliquots of 5 μL were analysed on 2% agarose gels and MDE heteroduplex analysis was performed according to the manufacturer's recommendation (AT Biochemicals). Heteroduplexes were visualized by staining with ethidium bromide. If a band of altered mobility was detected in heteroduplex analysis, the PCR product was subcloned into the TA vector (Invitrogen), and sequenced by standard techniques.

DNA isolated either from fibroblast cultures or from specimens obtained from buccal smears, was used as template for amplification of genomic sequences. For amplification of introns 8 and 16,~500 ng of genomic DNA was used as template and the following oligomer primers were utilized.

```
5' GGCTCACCAAGACTTACACA 3';

5' GAATCACTGAGCAGCTGAAC 3';

5' CAGTACCAGAACCGAGTTCG 3';

5' CTGGTTACCAGGCTTGAGAG 3';

5' TTACTGCGGAATCTCACAGC 3';

5' TACACTGTTCAACCCAGGGT 3';

5' AAACAAGCCCTCTCACTGGT 3';

5' GCGGAGACTGTGCTGATAAG 3';

5' CATACCTCTCTACATGGCAT 3';
```

```
5' AGTCTCGCTGAATCTCTCTT 3';

5' TTACAACTAGCATGGTGCCC 3'.
```

Amplification conditions were 94 C. for 7 min followed by 95 C. for 1.5 min, 56 C. (intron 8) or 58 C. (intron 16) for 1 min and 72 C. for 1.5 min for 35 cycles in an OmniGene thermal cycler (Marsh Scientific). Amplification was performed in a total volume of 25 µL containing 1.5 mM $MgCl_2$, and 2 U Taq polymerase (Boehringer Mannheim). The PCR products were subcloned and sequenced as above.

Verification of Mutations

The putative mutations detected in the PCR products were verified at the genomic level in both cases. For this purpose, a search for a potential change in restriction endonuclease sites as a result of the mutation was performed.

Amplification conditions were 94 C. for 7 min followed by 94 C. for 1 min, 58 C. for 45 sec and 72 C. for 45 sec for 35 cycles in an OmniGene thermal cycler (Marsh Scientific). PCR products were analysed on 2.5% agarose gels.

The methods described allow for the screening of patients for mutations in the γ2 chain which will correlate with JEB. As demonstrated, the results have identified a homozygous point mutation resulting in exon skipping, and a heterozygous deletion-insertion mutation. This demonstrating the effective screening for, and identification of, γ2 chain mutations which correlate with JEB. The methods are thus useful for diagnosis, prenatal screening, early screening and detection, as well as detailed examination of JEB. Further, the results show that the functional role of γ2 chain expression in epithelial cells is important in determining proper intercellular connectivity, relating to the integrity of tissues and cell interactions.

EXAMPLE 2

Mutation in the γ2 Chain Gene LAMC2 is Critical in H-JEB

The correlation both in vivo and in vitro of the dermo-epidermal separation in H-JEB, with deficient immunoreactivity of anti-nicein/kalinin/laminin 5 antibodies, and the separation induced by anti-nicein/kalinin/laminin 5 antibodies have made the genes encoding this protein strong candidates for the site of H-JEB mutations. In this example, it is demonstrated that the molecular defect which causes H-JEB is linked to the gene encoding nicein/kalinin/laminin 5 γ2 chain. In particular, the occurrence of a homozygous premature termination codon mutation is the specific cause in an examined case of H-JEB (Aberdam et al., *Nature Genetics*, 1994, 6:299–304).

Expression of mRNA encoding the three nicein subunits by northern analysis of RNA isolated from primary keratinocyte culture of a H-JEB patient was determined as the initial screen. Hybridization with probes for the α3 and α3 subunits was normal, but no hybridization with a cDNA encoding the γ2 subunit was detected. Examination of the genomic DNA for gross abnormalities, such as large deletions, insertions or rearrangements, in LAMC2 (the γ2 subunit gene) by Southern blot analysis turned up no abnormalities when the genomic DNA was digested with BamHI, BglI, HindIII, PstI or PvuII and probed with full length LAMC2 cDNA.

Possible mutations in the γ2 subunit were sought by using cDNA reverse transcribed from total RNA purified from cultured keratinocytes of the H-JEB patient, and subjected to PCR amplification. The size of the amplified products was checked by electrophoresis on 2% agarose gels and compared with that obtained from healthy controls.

No major differences were detected in the agarose gels, and the PCR products were examined by heteroduplex analysis (MDE). Heteroduplex analysis of the most 5' PCR product (nt 35–726) revealed the presence of a homoduplex in the proband (patient) and the controls. However, when the amplified PCR products from the patient and control were mixed together, an additional band with altered mobility, representing heteroduplexes, was detected, suggesting a homozygous mutation in the patient's LAMC2 cDNA (FIG. 5a). This amplified fragment corresponded to domain V of the γ2 protein (Vailly et al., *Eur. J. Biochem.*, 1994, 219:209–218). Sequencing detected a C to T transition at position +283, leading to a nonsense mutation in which a termination codon TGA replaces an arginine (CGA), perhaps arising as a result of the hypermutability of 5-methyl-cytosine to thymine at CpG nucleotides. This mutation, R95X, leads to truncation of the γ2 subunit polypeptide at amino acid 95 and loss of a TaqI restriction site (TCGA). Digestion of cDNA with TaqI confirmed the presence of a homozygous mutation in the DNA of the H-JEB patient. No other mutations were detected.

To confirm the cosegregation of the mutation with the loss of the TaqI restriction site, eight genotyped individuals of the family of the patient were screened. In each case, a 120 base pair fragment was amplified by PCR using genomic DNA templates and primers flanking the restriction site. Upon digestion of the wild type amplification product, two cleavage fragments of 80 and 40 base pairs are generated. Consistent with the presence of a heterozygous mutation in carriers of this genotype, DNA fragments of 120, 80 and 40 base pairs, indicative of a wild type genotype, were found in the paternal grandmother and two other relatives.

Cell Culture

Epidermis was separated from dermis by dispase treatment at 37 C. Keratinocytes were dissociated in 0.25% trypsin at 37 C. and plated onto a feeder layer of irradiated mouse 3T3 cells (ICN) (Rheinwald & Green, *Cell*, 175, 6:331–334). Keratinocytes were grown in a 1:1 mixture of DMEM and Ham's F12 (BRL) containing 10% Fetal Calf Serum (FCS), 1 mM sodium pyruvate, 2 mM L-glutamine, 10 µg/mL of penicillin and strptomycin, 10 ng/mL transferrin, 180 µM adenine and 20 pM T3 (Simon & Green, *Cell*, 1985, 40:677–683). H-JEB keratinocytes were expanded after gentle dissociation in 0.05% trypsin, 0.02% EDTA.

Northern Blot Analysis

Total RNA was prepared from H-JEB and normal cultured keratinocytes according to standard methods (Chomzynski & Sacchi, *Anal. Biochem.*, 1987, 162:156–159). RNA was electrophoresed in 1.2% denaturing agarose gels containing 1.2 M formaldehyde and transferred onto Hybond N membrane (Amersham). Membranes were hybridized at high stringency with P-32 labeled cDNA probes corresponding to the different chains of nicein, and then exposed on Hyperfilm MP (Amersham) with intensifying screens. Radiolabeled cDNA probes NA1 (Baudoin et al., *J. Invest. Dermatol.*, 1994, in press), KAL-5.5C (Gerecke et al., *Eur. J. Biochem.*, 1994, in press), and PCR 1.3 (Vailly et al., 1994, supra.), were used to detect the mRNAs for nicein chains α3, β3 and γ2, respectively.

RT-PCR and Heteroduplex Analysis (MDE)

50 µg of total RNA isolated from cultured keratinocytes from JEB patient, and unrelated healthy controls were reverse transcribed in a volume of 100 μL as recommended by the manufacturer (BRL). 1 μL of the reaction product was used to amplify overlapping regions of the cDNA that spanned the open reading frame. Primer pair used to identify the mutation R95X: (L) 5'-GAGCGCAGAGTGAGAACCAC-3', (R) 5'-ACTGTATTCTGCAGAGCTGC-3'. PCR cycling conditions were: 94 C., 5 min, followed by 94 C., 45 sec; 60 C., 45 sec; 72 C., 45 sec; for 35 cycles, and extension at 72 C. for 5 min. 5 μL aliquots were run in 2% agarose gels. Heteroduplex analysis was performed as recommended by the manufacturer (MDE, AT Biochemicals). Heteroduplexes were visualized under UV light in the presence of ethidium bromide and photographed. Amplified cDNA fragments with altered mobility were subcloned into the TA vector according to the manufacturer's recommendations (Invitrogen). Sequence analysis were then performed using standard techniques.

Verification of the Mutation

PCR reactions on genomic DNA (50 μg) were carried out using the upstream primer 5'-TTCCTTCCCCTACCTTGTG-3' and the downstream primer 5'-TGTGGAAGCCTGGCAGACAT-3', which are located in the intron 2 and exon 3 of LAMC2 respectively. PCR conditions were: 95 C., 5 min, followed by 94 C., 45 sec; 56 C., 45 sec; 72 C., 45 sec; for 35 cycles, and extension at 72 C. for 5 min. PCR products were used for restriction analysis. 20 μL of PCR product obtained from genomic DNA was digested with TaqI for 2 hours (Boehringer Mannheim). Clevage products were electrophoresed (2.4% agarose) stained and visualized under UV light.

Thus the methods allow for the screening of patients for mutations in the γ2 chain which correlate with H-JEB. As demonstrated, the results have identified a nonsense mutation resulting in a truncated γ2 chain, leading to severe H-JEB. This was further confirmed by specific amplification and restriction enzyme analysis of both the patient and relatives. Thus demonstrating the effective screening for, and identification of, γ2 chain mutations which correlate with H-JEB. The methods are thus useful for diagnosis, prenatal screening, early screening and detection, as well as detailed examination of H-JEB. Furthermore, the results demonstrate the significance of the γ2 chain in forming proper cellular contacts.

EXAMPLE 3

γ2 Chain as Diagnostic for Invasive Tissues

In this example, in situ hybridization is used to demonstrate the expression of the kalinin/laminin 5 γ2 chain in a variety of human cancer tissues and in skin wound healing in mice (Pyke et al., *Amer. J. Pathol.*, October 1994, 145(4): 1–10 in press).

Thirty-six routinely processed, formalin-fixed and paraffin wax-embedded specimens from cancer surgery performed from 1991 to 1993 were drawn from pathology department files at Herlev Hospital (Copenhagen, Denmark). The specimens were evaluated according to standard criteria and included 16 cases of moderately or well-differentiated colon adenocarcinomas, 7 cases of ductal mammary carcinomas, 4 squamous cell carcinomas (2 skin, 1 cervix, 1 vulva), 3 malignant melanomas, and 6 sarcomas (3 leiomyosarcomas, 2 malignant fibrous histiocytomas, 1 neurofibrosarcoma).

All samples were selected upon histological examination of a hematoxylin and eosin-stained section to ensure that they showed a well preserved morphology throughout and contained representative areas of both cancerous tissue and surrounding apparently normal, unaffected tissue. The broad zone separating these two tissue compartments is referred to as the invasive front in the following. No estimation of the effect of variations in fixation conditions was attempted, but in a previous study of plasminogen activating system components using specimens of colon adenocarcinomas collected using the same procedures, very little variation in relative mRNA levels was found (Pyke, C. PhD. Thesis, 1993, University of Copenhagen, Denmark). In addition, tissue from incisionally wounded mouse skin prepared as described by Romer et al. (*J. Invest. Dermatol.*, 1994, 102:519–522), was fixed and paraffin-embedded the same way as the human cancer specimens.

For preparation of total RNA from six samples of colon adenocarcinomas, tissues were snap-frozen in liquid nitrogen immediately following resection and RNA was prepared as described by Lund et al., (*Biochem. J.*, 1994, in press).

Probes

Fragments of the cDNA for the γ2 chain of human kalinin/laminin 5 was inserted into RNA transcription vectors by restriction enzyme cutting of clone L15 covering base pairs 2995 to 3840 (FIG. 4; Kallunki et al., 1992, supra.). In brief, plasmids phb2t-01 and phb2t-02 were prepared by insertion of the complete L15 γ2 chain cDNA in sense and anti-sense orientation into the polylinker of plasmid vectors SP64 and SP65 (both Promega, Madison, Wis.), respectively. In addition, two non-overlapping fragments of clone L15 were bluntend cloned into the EcoRV-site of pKS(Bluescript)II(+) (Stratagene, La Jolla, Calif.) transcription vector and the resulting plasmids were verified by dideoxy sequencing according to Sanger et al (*PNAS(USA)*, 1977, 74:5463–5471). Plasmid phb2t-03 cover bases 3003–3239 and phb2t-05 cover bases 3239 to 3839, numbers referring to cDNA sequence Z15008 in the EMBL/GenBank/DDBJ database as reported by Kallunki et al., (1992, supra.; FIG. 4).

Similarly, cDNA fragments of other human laminin chains were prepared in RNA transcription vectors, yielding the following plasmid constructs (numbers in brackets refer to base pair numbers in the EMBL/GenBank/DDBJ sequence database by the listed accession numbers); chain α1: plasmid phae-01 (3244–3584 (accession No. X58531, Nissinen et al., *Biochem. J.*, 1991, 276:369–379) in pKS (Bluescript)II(+)); chain β1: plasmid phb1e-01 (3460–4366 (accession No. J02778, Pikkarainen et al., *J. Biol. Chem.*, 1987, 262:10454–10462) in pKS(Bluescript)II(+)); chain γ1: plasmids A1PSP64 and A1PSP65 (919–1535 (accession No. M55210, Pikkarainen et al., *J. Biol. Chem.*, 1988, 263:6751–6758) in SP64 and SP65 respectively (sense and anti-sense orientation)).

All plasmids were linearized for transcription using restriction endonucleases and 5 μg of the linearized plasmids was extracted with phenol and with chloroform/isoamyl alcohol (25:1), precipitated with ethanol, and redissolved in water. Each transcription reaction contained 1 μg linearized DNA template, and transcriptions were performed essentially as recommended by the manufacturer of the polymerases. The RNA was hydrolyzed in 0.1 mol/L sodium carbonate buffer, pH 10.2, containing 10 mmol/L dithiothreitol (DTT) to an average size of 100 bases. RNA probes transcribed from opposite strands of the same plasmid template, yielding sense and anti-sense transcripts, were adjusted to $1 \times 10^6$ cpm/μL and stored at −20 C. until used. Probes were applied to tissue sections.

In situ Hybridization

In situ Hybridization was performed as described by Pyke et al., (*Am. J. Pathol.*, 1991, 38:1059–1067) with $S^{35}$ labeled RNA probes prepared as described above. In brief, paraffin sections were cut, placed on gelatinized slides, heated to 60 C. for 30 minutes, deparaffinized in xylene, and rehydrated through graded alcohols to PBS (0.01 mol/L sodium phosphate buffer, pH 7.4, containing 0.14 mol/L NaCl). The slides were then washed twice in PBS, incubated with 5 μg/mL proteinase K in 50 mmol/L Tris/HCl, pH 8.0, with 5 mmol/L EDTA for 7.5 minutes, washed in PBS (2 minutes), dehydrated in graded ethanols, and air-dried before the RNA probe (~80 pg/μL) was applied. The hybridization solution consisted of deionized formamide (50%), dextran sulfate (10%), tRNA (1 μg/μL), Ficoll 400 (0.02% (w/v)), polyvinylpyrrolidone (0.02% (w/v)), BSA fraction V (0.02% (w/v)), 10 mmol/L DTT, 0.3 M NaCl, 0.5 mmol/L EDTA, 10 mmol/L Tris-HCl, and 10 mmol/L $NaPO_4$ (pH 6.8). Sections were covered by alcohol-washed, autoclaved coverslips and hybridized at 47 C. overnight (16 to 18 hours) in a chamber humidified with 10 ml of a mixture similar to the hybridization solution, except for the omission of probe, dextran sulfate, DTT, and tRNA (washing mixture). After hybridization, slides were washed in washing mixture for 2×1 hour at 50 C., followed by 0.5 mol/L NaCl, 1 mmol/L EDTA, 10 mmol/L Tris-HCl (pH 7.2) (NTE) with 10 mmol/L DTT at 37 C. for 15 minutes. After treatment with RNAse A (20 μg/mL) in NTE at 37 C. for 30 minutes, the sections were washed in NTE at 37 C. (2×30 minutes), and in 2 L of 15 mmol/L sodium chloride, 1.5 mmol/L sodium citrate, pH 7.0, with 1 mmol/L DTT for 30 minutes at room temperature with stirring. Sections were then dehydrated and air-dried. Finally, autoradiographic emulsion was applied according to the manufacturer's recommendations, and sections were stored in black airtight boxes at 4 C. until they were developed after 1 to 2 weeks of exposure.

Results: Laminin α1, β1, γ1, and γ2 chains

All rounds of in situr hybridization include both sense and anti-sense RNA probes for each of the genes studied. As negative controls, sense RNA probes are applied to adjacent sections and these probes consistently are negative. As a positive control of the γ2 chain hybridizations, two anti-sense probes derived from non-overlapping γ2 chain cDNA clones are used on a number of sections. To summarizes the γ2 chain expression found; all carcinomas were positive except for one case of mammary duct carcinoma, and all three cases of leiomyosarcomas, both cases of malignant fibrous histiocytoma, and the only case of neurofibrosarcoma. The positive controls always give similar staining on adjacent sections (see FIG. 2, E and G). Fifteen of the malignant cases and all mouse tissue blocks were hybridized on two or more separate occasions giving the same hybridization pattern. All cell types other than those described below were negative in all cases.

Colon Adenocarcinoma

Sixteen specimens of colon adenocarcinoma were investigated by in situ hybridization for expression of the γ2 chain (FIG. 1). In all of these cases, mRNA for γ2 chain was present exclusively in cancer cells and in most of the cases, staining was confined to a distinct subpopulation of cancer cells at the invasive front (FIG. 1, A–D). A characteristic feature of γ2 chain containing cancer cells at the invasive front was that they appeared to represent cells in the process of branching or dissociating from larger well differentiated epithelial glands, a phenomenon referred to in the literature as tumor budding or tumor-cell dissociation.

In normal-looking colon mucosa distal from the invasive carcinoma, moderate signals for γ2 chain mRNA were observed in two specimens in the epithelial cells of a few mucosal glands that showed clear morphological signs of glandular disintegration and phagocytic cell infiltration. Apart from this, a weak signal was seen in luminal epithelial cells in normal looking colon mucosa in most specimens.

Weak signals for laminin chains α1, β1, and γ1 mRNAs were detected in cancerous areas of the 6 colon cancers studied for the expression of these genes. The expression of each of the three genes showed a similar distribution. Expression in stromal cells with a fibroblast-like morphology as well as in endothelial cells of smaller vessels was consistently found. In marked contrast to the γ2 chain expression in the same samples, expression of α1, β1, or γ1 was never found in cancer cells and no correlation between expression of α1, β1, and γ1 chains with sites of invasion was found. Adjacent normal-looking parts of the samples were negative or only weakly positive for these laminin chains.

FIG. 1 shows In situ hybridization of a specimen of colon adenocarcinoma for γ2 chain mRNA using a S-35 labeled anti-sense RNA probe derived from plasmid pbb2r-02. FIG. 1A is a cluster of heavily labeled cancer cells at the invasive front (open arrow) in close proximity to a well-differentiated glandular structure (straight arrow). FIG. 1B shows a high-magnification view of the area at the open arrow in 1A. Note that the isolated cancer cells show prominent labeling, whereas many coherent cancer cells of an adjacent glandular structure are negative (straight arrow). FIG. 1C shows the same pattern at an invasive focus in another part of the same specimen. FIG. 1D shows strong γ2 chain expression in cancer cells engaged in a bifurcation process (curved arrows). The malignant glandular epithelium from which the γ2 chain-positive cancer cells are branching is negative (straight arrow). Magnification: 1A×100: 1B–1D×640.

Ductal Mammary Carcinomas

Six of the seven cases showed a prominent signal for γ2 chain in a small subpopulation of cells intimately associated with invasively growing malignant glandular structures. The most prominent signal was seen in cells located at the border between malignant and surrounding stromal tissue in glandular structures that exhibited clear histological signs of active invasion (FIG. 2A). On careful examination it was concluded that the majority of the positive cells were cancer cells but it was not possible to determine if the cells of myoepithelial origin were also positive in some cases. One case was totally negative. Normal-appearing glandular tissue was negative in all cases.

Weak signals for laminin chains α1, β1, and γ1 mRNAs were detected in fibroblast-like stromal cells throughout cancerous areas in one of the cases.

Malignant Melanoma

In all three cases strong hybridization of γ2 chain was found in a population of cancer cells in the radial growth phase (FIG. 2B). Laminin chains α1, β1, and γ1 were weakly expressed in the endothelium of small vessels and in fibroblast-like stromal cells throughout the affected areas in the two cases studied for these components. In addition, a weak signal for these chains was seen in sebaceous glands of adjacent normal skin.

Squamous Cell Carcinomas

In all four squamous cell carcinomas investigated, the same pattern of γ2 chain expression was found as in other carcinomas. The signals were found only in cancer cells, and only in areas with signs of ongoing invasion (FIG. 2, C–G).

The four cases were also studied for mRNA of α1, β1, and γ1 chains. In the two skin cancers, it was found that a very weak signal occurred in malignant cells, and that the weak signal was in all cancer cells and of an equal intensity. This is in clear contrast to the pattern of expression of the γ2 chain. As seen in melanomas, epithelial cells of sebaceous glands present in adjacent unaffected skin were weakly positive for these laminin chains. In the other two cases (cervix and vulva) weak expression of α1, β1, and γ1 chains were seen only in endothelial and fibroblast-like stromal cells throughout the cancerous areas (FIG. 2F).

FIG. 2 shows In situ hybridization for γ2 chain mRNA on sections of ductal mammary carcinoma (2A), malignant melanoma (2B), squamous cell carcinoma of the skin (2C–2D), and squamous cell carcinoma of the vulva (2E–2G). In 2A, cancer shows prominent signal for γ2 chain mRNA in cells bordering the zone between malignant glandular tissue and surrounding mesenchyme (curved arrows). Cancer cells located more centrally in individual malignant glandular structures are negative for γ2 chain mRNA (straight arrows). Note the wedge shaped form of the invading glandular tissue. (All images marked X' are darkfield images of the respective sections). FIG. 2B shows γ2 chain mRNA signal in a subpopulation of cancer cells of radially growing malignant epithelium (curved arrows). Adjacent malignant epithelium showing a different growth pattern is devoid signal (straight arrow). FIG. 2C shows γ2 chain mRNA containing cancer cells at the invasive front (curved arrow). Note lack of signal in non-invasive areas of the tumor and in adjacent unaffected areas (straight arrow). FIG. 2D is a higher magnification of area of curved arrow of 2C. highlighting the prominent signal in invading cells (curved arrow). Adjacent cancer cells with tumor islets are negative (straight arrow). FIG. 2E shows a strong signal for γ2 chain mRNA is seen in invading cancer cells, using an anti-sense RNA probe derived from plasmid pb2t-03 (curved arrow). A postcapillary venule is negative (straight arrow). FIG. 2F is a near adjacent section hybridized for laminin γ1 chain. Note that the endothelial cells of the venule show signal (straight arrow) whereas the malignant epithelium is negative (curved arrow). FIG. 2G is another near-adjacent section which was hybridized for γ2 chain expression using an anti-sense RNA probe derived from a cDNA plasmid non-overlapping with that used for preparing the probe in 2E (phb2t-05). Note that the hybridization patter is similar to that seen in 2E, with strong signal in invading cancer cells (curved arrow) and absence of signal in a vessel (straight arrow). Magnification: 2C×100, all others×640.

Sarcomas

All six sarcomas tested in the study were totally negative for γ2 chain mRNA. The expression of other laminin chains was not done.

Mouse Wounded Skin

To compare the gene expression of γ2 chain in cancer tissue with a nonmalignant condition known to contain actively migrating epithelial cells showing a transient invasive phenotype, we hybridized sections of incisionally wounded mouse skin with γ2 chain sense and anti-sense RNA probes. Weak γ2 chain expression was observed in the keratinocytes at the edge of 12-hour old wounds, and at later time points (1–5 days), strong signals for γ2 chain mRNA was seen exclusively in the basal keratinocytes of the epidermal tongue moving under the wound clot (FIG. 3). In adjacent normal-looking skin, keratinocytes were negative for γ2 chain mRNA.

FIG. 3 is incisionally wounded mouse skin (72 hours after wounding) showing signal for γ2 chain in keratinocytes at the leading edge of the migrating epithelium (curved arrow). Whereas buccal keratinocytes located more distant to the site of injury show little or no signal (straight arrow). Note that the signal for γ2 chain stops at the tip of invading keratinocytes (open arrow). A' is a dark field image of 2A. Magnification:×640.

RNAse Protection Assay

Plasmid phbt-03 was linearized with EcoRI and a radio-labeled RNA-anti-sense probe was prepared by transcription using P-32 UTP and T3 polymerase (Pyke et al., *FEBS Letters*, 1993, 326:69–75). RNAse protection assay, using 40 μg ethanol-precipitated and DNAse I-treated total RNA from six samples of colon adenocarcinomas was performed as described in Pyke et al., (1993, supra.). Protected mRNA regions were analyzed on a denaturing polyacrylamide gel and autoradiography.

The RNAse protection assay carried out on total RNA from the six samples confirmed the presence of genuine γ2 chain mRNA in all samples.

These results clearly demonstrate the important correlation of γ2 chain expression and invasive cell phenotype in vivo, as detected in vitro. Thus the instant methods present a novel and important method for the specific identification of invasive cell phenotypes in biopsied tissues. The knowledge of any information diagnostic for the presence or absence of invasive cells is useful for the monitoring and prognosis of continuing anti-carcinoma therapies. Further the identification of the expression or non-expression of the γ2 chain provides important information as to the phenotypic nature of the tissue expanded. Thus the instant example demonstrates the use of probes of γ2 chain for detection of the presence, or absence, of invasive cells.

Those skilled in the art will know, or be able to ascertain, using no more than routine experimentation, many equivalents to the specific embodiments of the invention described herein. These and all other equivalents are intended to be encompassed by the following claims.

We claim:

1. A method for determining the presence of invasive cells in a tumor tissue by detecting the presence of laminin 5 gamma-2 chain protein in said tumor tissue, comprising contacting said tumor tissue with an antibody which specifically binds to the gamma-2 chain of said laminin 5 protein to form an immunocomplex, and detecting formation of any immunocomplex, wherein said formation of said immunocomplex correlates with the presence of said invasive cells in said tumor tissue.

2. A method for determining the presence of invasive cells in a colon carcinoma by detecting the presence of laminin 5 gamma-2 chain protein in said colon carcinoma, comprising contacting said colon carcinoma with an antibody which specifically binds to the gamma-2 chain of said laminin 5 protein to form an immunocomplex, and detecting formation of any immunocomplex, wherein said formation of said immunocomplex correlates with the presence of said invasive cells in said colon carcinoma.

3. A method for determining the presence of invasive cells in a squamous cell carcinoma by detecting the presence of laminin 5 gamma-2 chain protein in said squamous cell carcinoma, comprising contacting said squamous cell carcinoma with an antibody which specifically binds to the gamma-2 chain of said laminin 5 protein to form an immunocomplex, and detecting formation of any immunocomplex, wherein said formation of said immunocomplex correlates with the presence of said invasive cells in said squamous cell carcinoma.

4. The method of claim 3 wherein the squamous cell carcinoma is selected from the group consisting of squamous cell carcinoma of skin, cervix, and vulva.

\* \* \* \* \*

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
                (A) DESCRIPTION: /desc = "oligomer primers"

(xi) SEQUENCE DESCRIPTION: SEQ ID NO:1:

GGCTCACCAA GACTTACACA                                                        20

(2) INFORMATION FOR SEQ ID NO:2:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "OLIGOMER PRIMER"

(xi) SEQUENCE DESCRIPTION: SEQ ID NO:2:

GAATCACTGA GCAGCTGAAC                                                        20

(2) INFORMATION FOR SEQ ID NO:3:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "OLIGOMER PRIMER"

(xi) SEQUENCE DESCRIPTION: SEQ ID NO:3:

CAGTACCAGA ACCGAGTTCG                                                        20

(2) INFORMATION FOR SEQ ID NO:4:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "OLIGOMER PRIMER"

(xi) SEQUENCE DESCRIPTION: SEQ ID NO:4:

CTGGTTACCA GGCTTGAGAG                                                        20

(2) INFORMATION FOR SEQ ID NO:5:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "OLIGOMER PRIMER"

(xi) SEQUENCE DESCRIPTION: SEQ ID NO:5:

TTACTGCGGA ATCTCACAGC                                                        20

(2) INFORMATION FOR SEQ ID NO:6:

(i) SEQUENCE CHARACTERISTICS:
                (A) LENGTH: 20 base pairs
                (B) TYPE: nucleic acid
                (C) STRANDEDNESS: single -continued

```
          (D) TOPOLOGY: linear (ii) MOLECULE TYPE: other nucleic acid
          (A) DESCRIPTION: /desc = "OLIGOMER PRIMER"

(xi) SEQUENCE DESCRIPTION: SEQ ID NO:6:

TACACTGTTC AACCCAGGGT                                         20

(2) INFORMATION FOR SEQ ID NO:7:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "OLIGOMER PRIMER"

(xi) SEQUENCE DESCRIPTION: SEQ ID NO:7:

AAACAAGCCC TCTCACTGGT                                         20

(2) INFORMATION FOR SEQ ID NO:8:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "OLIGOMER PRIMER"

(xi) SEQUENCE DESCRIPTION: SEQ ID NO:8:

GCGGAGACTG TGCTGATAAG                                         20

(2) INFORMATION FOR SEQ ID NO:9:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "OLIGOMER PRIMER"

(xi) SEQUENCE DESCRIPTION: SEQ ID NO:9:

CATACCTCTC TACATGGCAT                                         20

(2) INFORMATION FOR SEQ ID NO:10:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "OLIGOMER PRIMER"

(xi) SEQUENCE DESCRIPTION: SEQ ID NO:10:

AGTCTCGCTG AATCTCTCTT                                         20

(2) INFORMATION FOR SEQ ID NO:11:

(i) SEQUENCE CHARACTERISTICS:
          (A) LENGTH: 20 base pairs
          (B) TYPE: nucleic acid
```

```
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO:11:

TTACAACTAG CATGGTGCCC                                                  20

(2) INFORMATION FOR SEQ ID NO:12:

(i) SEQUENCE CHARACTERISTICS:
        (A) LENGTH: 5200 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: sig_peptide
        (B) LOCATION: 118..183

(ix) FEATURE:
        (A) NAME/KEY: CDS
        (B) LOCATION: 118..3699

(ix) FEATURE:
        (A) NAME/KEY: polyA_site
        (B) LOCATION: 4433

(ix) FEATURE:
        (A) NAME/KEY: polyA_site
        (B) LOCATION: 5195

(xi) SEQUENCE DESCRIPTION: SEQ ID NO:12:
```

```
GACCACCTGA TCGAAGGAAA AGGAAGGCAC AGCGGAGCGC AGAGTGAGAA CCACCAACCG          60

AGGCGCCGGG CAGCGACCCC TGCAGCGGAG ACAGAGACTG AGCGGCCCGG CACCGCC            117

ATG CCT GCG CTC TGG CTG GGC TGC TGC CTC TGC TTC TCG CTC CTC CTG           165
Met Pro Ala Leu Trp Leu Gly Cys Cys Leu Cys Phe Ser Leu Leu Leu
 1               5                  10                  15

CCC GCA GCC CGG GCC ACC TCC AGG AGG GAA GTC TGT GAT TGC AAT GGG           213
Pro Ala Ala Arg Ala Thr Ser Arg Arg Glu Val Cys Asp Cys Asn Gly
             20                  25                  30

AAG TCC AGG CAG TGT ATC TTT GAT CGG GAA CTT CAC AGA CAA ACT GGT           261
Lys Ser Arg Gln Cys Ile Phe Asp Arg Glu Leu His Arg Gln Thr Gly
         35                  40                  45

AAT GGA TTC CGC TGC CTC AAC TGC AAT GAC AAC ACT GAT GGC ATT CAC           309
Asn Gly Phe Arg Cys Leu Asn Cys Asn Asp Asn Thr Asp Gly Ile His
     50                  55                  60

TGC GAG AAG TGC AAG AAT GGC TTT TAC CGG CAC AGA GAA AGG GAC CGC           357
Cys Glu Lys Cys Lys Asn Gly Phe Tyr Arg His Arg Glu Arg Asp Arg
 65                  70                  75                  80

TGT TTG CCC TGC AAT TGT AAC TCC AAA GGT TCT CTT AGT GCT CGA TGT           405
Cys Leu Pro Cys Asn Cys Asn Ser Lys Gly Ser Leu Ser Ala Arg Cys
                 85                  90                  95

GAC AAC TCT GGA CGG TGC AGC TGT AAA CCA GGT GTG ACA GGA GCC AGA           453
Asp Asn Ser Gly Arg Cys Ser Cys Lys Pro Gly Val Thr Gly Ala Arg
            100                 105                 110

TGC GAC CGA TGT CTG CCA GGC TTC CAC ATG CTC ACG GAT GCG GGG TGC           501
Cys Asp Arg Cys Leu Pro Gly Phe His Met Leu Thr Asp Ala Gly Cys
        115                 120                 125

ACC CAA GAC CAG AGA CTG CTA GAC TCC AAG TGT GAC TGT GAC CCA GCT           549
Thr Gln Asp Gln Arg Leu Leu Asp Ser Lys Cys Asp Cys Asp Pro Ala
    130                 135                 140
```

```
GGC ATC GCA GGG CCC TGT GAC GCG GGC CGC TGT GTC TGC AAG CCA GCT      597
Gly Ile Ala Gly Pro Cys Asp Ala Gly Arg Cys Val Cys Lys Pro Ala
145                 150                 155                 160

GTT ACT GGA GAA CGC TGT GAT AGG TGT CGA TCA GGT TAC TAT AAT CTG      645
Val Thr Gly Glu Arg Cys Asp Arg Cys Arg Ser Gly Tyr Tyr Asn Leu
                165                 170                 175

GAT GGG GGG AAC CCT GAG GGC TGT ACC CAG TGT TTC TGC TAT GGG CAT      693
Asp Gly Gly Asn Pro Glu Gly Cys Thr Gln Cys Phe Cys Tyr Gly His
            180                 185                 190

TCA GCC AGC TGC CGC AGC TCT GCA GAA TAC AGT GTC CAT AAG ATC ACC      741
Ser Ala Ser Cys Arg Ser Ser Ala Glu Tyr Ser Val His Lys Ile Thr
        195                 200                 205

TCT ACC TTT CAT CAA GAT GTT GAT GGC TGG AAG GCT GTC CAA CGA AAT      789
Ser Thr Phe His Gln Asp Val Asp Gly Trp Lys Ala Val Gln Arg Asn
    210                 215                 220

GGG TCT CCT GCA AAG CTC CAA TGG TCA CAG CGC CAT CAA GAT GTG TTT      837
Gly Ser Pro Ala Lys Leu Gln Trp Ser Gln Arg His Gln Asp Val Phe
225                 230                 235                 240

AGC TCA GCC CAA CGA CTA GAT CCT GTC TAT TTT GTG GCT CCT GCC AAA      885
Ser Ser Ala Gln Arg Leu Asp Pro Val Tyr Phe Val Ala Pro Ala Lys
                245                 250                 255

TTT CTT GGG AAT CAA CAG GTG AGC TAT GGG CAA AGC CTG TCC TTT GAC      933
Phe Leu Gly Asn Gln Gln Val Ser Tyr Gly Gln Ser Leu Ser Phe Asp
            260                 265                 270

TAC CGT GTG GAC AGA GGA GGC AGA CAC CCA TCT GCC CAT GAT GTG ATC      981
Tyr Arg Val Asp Arg Gly Gly Arg His Pro Ser Ala His Asp Val Ile
        275                 280                 285

CTG GAA GGT GCT GGT CTA CGG ATC ACA GCT CCC TTG ATG CCA CTT GGC     1029
Leu Glu Gly Ala Gly Leu Arg Ile Thr Ala Pro Leu Met Pro Leu Gly
    290                 295                 300

AAG ACA CTG CCT TGT GGG CTC ACC AAG ACT TAC ACA TTC AGG TTA AAT     1077
Lys Thr Leu Pro Cys Gly Leu Thr Lys Thr Tyr Thr Phe Arg Leu Asn
305                 310                 315                 320

GAG CAT CCA AGC AAT AAT TGG AGC CCC CAG CTG AGT TAC TTT GAG TAT     1125
Glu His Pro Ser Asn Asn Trp Ser Pro Gln Leu Ser Tyr Phe Glu Tyr
                325                 330                 335

CGA AGG TTA CTG CGG AAT CTC ACA GCC CTC CGC ATC CGA GCT ACA TAT     1173
Arg Arg Leu Leu Arg Asn Leu Thr Ala Leu Arg Ile Arg Ala Thr Tyr
            340                 345                 350

GGA GAA TAC AGT ACT GGG TAC ATT GAC AAT GTG ACC CTG ATT TCA GCC     1221
Gly Glu Tyr Ser Thr Gly Tyr Ile Asp Asn Val Thr Leu Ile Ser Ala
        355                 360                 365

CGC CCT GTC TCT GGA GCC CCA GCA CCC TGG GTT GAA CAG TGT ATA TGT     1269
Arg Pro Val Ser Gly Ala Pro Ala Pro Trp Val Glu Gln Cys Ile Cys
    370                 375                 380

CCT GTT GGG TAC AAG GGG CAA TTC TGC CAG GAT TGT GCT TCT GGC TAC     1317
Pro Val Gly Tyr Lys Gly Gln Phe Cys Gln Asp Cys Ala Ser Gly Tyr
385                 390                 395                 400

AAG AGA GAT TCA GCG AGA CTG GGG CCT TTT GGC ACC TGT ATT CCT TGT     1365
Lys Arg Asp Ser Ala Arg Leu Gly Pro Phe Gly Thr Cys Ile Pro Cys
                405                 410                 415

AAC TGT CAA GGG GGA GGG GCC TGT GAT CCA GAC ACA GGA GAT TGT TAT     1413
Asn Cys Gln Gly Gly Gly Ala Cys Asp Pro Asp Thr Gly Asp Cys Tyr
            420                 425                 430

TCA GGG GAT GAG AAT CCT GAC ATT GAG TGT GCT GAC TGC CCA ATT GGT     1461
Ser Gly Asp Glu Asn Pro Asp Ile Glu Cys Ala Asp Cys Pro Ile Gly
        435                 440                 445

TTC TAC AAC GAT CCG CAC GAC CCC CGC AGC TGC AAG CCA TGT CCC TGT     1509
Phe Tyr Asn Asp Pro His Asp Pro Arg Ser Cys Lys Pro Cys Pro Cys
    450                 455                 460
```

-continued

| | |
|---|---|
| CAT AAC GGG TTC AGC TGC TCA GTG ATT CCG GAG ACG GAG GAG GTG GTG<br>His Asn Gly Phe Ser Cys Ser Val Ile Pro Glu Thr Glu Glu Val Val<br>465                    470                 475                  480 | 1557 |
| TGC AAT AAC TGC CCT CCC GGG GTC ACC GGT GCC CGC TGT GAG CTC TGT<br>Cys Asn Asn Cys Pro Pro Gly Val Thr Gly Ala Arg Cys Glu Leu Cys<br>                   485                  490                  495 | 1605 |
| GCT GAT GGC TAC TTT GGG GAC CCC TTT GGT GAA CAT GGC CCA GTG AGG<br>Ala Asp Gly Tyr Phe Gly Asp Pro Phe Gly Glu His Gly Pro Val Arg<br>               500                  505                 510 | 1653 |
| CCT TGT CAG CCC TGT CAA TGC AAC AGC AAT GTG GAC CCC AGT GCC TCT<br>Pro Cys Gln Pro Cys Gln Cys Asn Ser Asn Val Asp Pro Ser Ala Ser<br>       515                  520                  525 | 1701 |
| GGG AAT TGT GAC CGG CTG ACA GGC AGG TGT TTG AAG TGT ATC CAC AAC<br>Gly Asn Cys Asp Arg Leu Thr Gly Arg Cys Leu Lys Cys Ile His Asn<br>530                    535                 540 | 1749 |
| ACA GCC GGC ATC TAC TGC GAC CAG TGC AAA GCA GGC TAC TTC GGG GAC<br>Thr Ala Gly Ile Tyr Cys Asp Gln Cys Lys Ala Gly Tyr Phe Gly Asp<br>545                    550                 555                 560 | 1797 |
| CCA TTG GCT CCC AAC CCA GCA GAC AAG TGT CGA GCT TGC AAC TGT AAC<br>Pro Leu Ala Pro Asn Pro Ala Asp Lys Cys Arg Ala Cys Asn Cys Asn<br>                   565                  570                  575 | 1845 |
| CCC ATG GGC TCA GAG CCT GTA GGA TGT CGA AGT GAT GGC ACC TGT GTT<br>Pro Met Gly Ser Glu Pro Val Gly Cys Arg Ser Asp Gly Thr Cys Val<br>               580                  585                 590 | 1893 |
| TGC AAG CCA GGA TTT GGT GGC CCC AAC TGT GAG CAT GGA GCA TTC AGC<br>Cys Lys Pro Gly Phe Gly Gly Pro Asn Cys Glu His Gly Ala Phe Ser<br>       595                  600                  605 | 1941 |
| TGT CCA GCT TGC TAT AAT CAA GTG AAG ATT CAG ATG GAT CAG TTT ATG<br>Cys Pro Ala Cys Tyr Asn Gln Val Lys Ile Gln Met Asp Gln Phe Met<br>610                    615                 620 | 1989 |
| CAG CAG CTT CAG AGA ATG GAG GCC CTG ATT TCA AAG GCT CAG GGT GGT<br>Gln Gln Leu Gln Arg Met Glu Ala Leu Ile Ser Lys Ala Gln Gly Gly<br>625                    630                 635                 640 | 2037 |
| GAT GGA GTA GTA CCT GAT ACA GAG CTG GAA GGC AGG ATG CAG CAG GCT<br>Asp Gly Val Val Pro Asp Thr Glu Leu Glu Gly Arg Met Gln Gln Ala<br>                   645                  650                  655 | 2085 |
| GAG CAG GCC CTT CAG GAC ATT CTG AGA GAT GCC CAG ATT TCA GAA GGT<br>Glu Gln Ala Leu Gln Asp Ile Leu Arg Asp Ala Gln Ile Ser Glu Gly<br>               660                  665                 670 | 2133 |
| GCT AGC AGA TCC CTT GGT CTC CAG TTG GCC AAG GTG AGG AGC CAA GAG<br>Ala Ser Arg Ser Leu Gly Leu Gln Leu Ala Lys Val Arg Ser Gln Glu<br>       675                  680                  685 | 2181 |
| AAC AGC TAC CAG AGC CGC CTG GAT GAC CTC AAG ATG ACT GTG GAA AGA<br>Asn Ser Tyr Gln Ser Arg Leu Asp Asp Leu Lys Met Thr Val Glu Arg<br>690                    695                 700 | 2229 |
| GTT CGG GCT CTG GGA AGT CAG TAC CAG AAC CGA GTT CGG GAT ACT CAC<br>Val Arg Ala Leu Gly Ser Gln Tyr Gln Asn Arg Val Arg Asp Thr His<br>705                    710                 715                 720 | 2277 |
| AGG CTC ATC ACT CAG ATG CAG CTG AGC CTG GCA GAA AGT GAA GCT TCC<br>Arg Leu Ile Thr Gln Met Gln Leu Ser Leu Ala Glu Ser Glu Ala Ser<br>                   725                  730                  735 | 2325 |
| TTG GGA AAC ACT AAC ATT CCT GCC TCA GAC CAC TAC GTG GGG CCA AAT<br>Leu Gly Asn Thr Asn Ile Pro Ala Ser Asp His Tyr Val Gly Pro Asn<br>               740                  745                 750 | 2373 |
| GGC TTT AAA AGT CTG GCT CAG GAG GCC ACA AGA TTA GCA GAA AGC CAC<br>Gly Phe Lys Ser Leu Ala Gln Glu Ala Thr Arg Leu Ala Glu Ser His<br>       755                  760                  765 | 2421 |
| GTT GAG TCA GCC AGT AAC ATG GAG CAA CTG ACA AGG GAA ACT GAG GAC<br>Val Glu Ser Ala Ser Asn Met Glu Gln Leu Thr Arg Glu Thr Glu Asp | 2469 |

```
                770                 775                 780
TAT TCC AAA CAA GCC CTC TCA CTG GTG CGC AAG GCC CTG CAT GAA GGA          2517
Tyr Ser Lys Gln Ala Leu Ser Leu Val Arg Lys Ala Leu His Glu Gly
785                 790                 795                 800

GTC GGA AGC GGA AGC GGT AGC CCG GAC GGT GCT GTG GTG CAA GGG CTT          2565
Val Gly Ser Gly Ser Gly Ser Pro Asp Gly Ala Val Val Gln Gly Leu
                    805                 810                 815

GTG GAA AAA TTG GAG AAA ACC AAG TCC CTG GCC CAG CAG TTG ACA AGG          2613
Val Glu Lys Leu Glu Lys Thr Lys Ser Leu Ala Gln Gln Leu Thr Arg
            820                 825                 830

GAG GCC ACT CAA GCG GAA ATT GAA GCA GAT AGG TCT TAT CAG CAC AGT          2661
Glu Ala Thr Gln Ala Glu Ile Glu Ala Asp Arg Ser Tyr Gln His Ser
            835                 840                 845

CTC CGC CTC CTG GAT TCA GTG TCT CCG CTT CAG GGA GTC AGT GAT CAG          2709
Leu Arg Leu Leu Asp Ser Val Ser Pro Leu Gln Gly Val Ser Asp Gln
        850                 855                 860

TCC TTT CAG GTG GAA GAA GCA AAG AGG ATC AAA CAA AAA GCG GAT TCA          2757
Ser Phe Gln Val Glu Glu Ala Lys Arg Ile Lys Gln Lys Ala Asp Ser
865                 870                 875                 880

CTC TCA AGC CTG GTA ACC AGG CAT ATG GAT GAG TTC AAG CGT ACA CAA          2805
Leu Ser Ser Leu Val Thr Arg His Met Asp Glu Phe Lys Arg Thr Gln
                    885                 890                 895

AAG AAT CTG GGA AAC TGG AAA GAA GAA GCA CAG CAG CTC TTA CAG AAT          2853
Lys Asn Leu Gly Asn Trp Lys Glu Glu Ala Gln Gln Leu Leu Gln Asn
            900                 905                 910

GGA AAA AGT GGG AGA GAG AAA TCA GAT CAG CTG CTT TCC CGT GCC AAT          2901
Gly Lys Ser Gly Arg Glu Lys Ser Asp Gln Leu Leu Ser Arg Ala Asn
            915                 920                 925

CTT GCT AAA AGC AGA GCA CAA GAA GCA CTG AGT ATG GGC AAT GCC ACT          2949
Leu Ala Lys Ser Arg Ala Gln Glu Ala Leu Ser Met Gly Asn Ala Thr
        930                 935                 940

TTT TAT GAA GTT GAG AGC ATC CTT AAA AAC CTC AGA GAG TTT GAC CTG          2997
Phe Tyr Glu Val Glu Ser Ile Leu Lys Asn Leu Arg Glu Phe Asp Leu
945                 950                 955                 960

CAG GTG GAC AAC AGA AAA GCA GAA GCT GAA GAA GCC ATG AAG AGA CTC          3045
Gln Val Asp Asn Arg Lys Ala Glu Ala Glu Glu Ala Met Lys Arg Leu
                    965                 970                 975

TCC TAC ATC AGC CAG AAG GTT TCA GAT GCC AGT GAC AAG ACC CAG CAA          3093
Ser Tyr Ile Ser Gln Lys Val Ser Asp Ala Ser Asp Lys Thr Gln Gln
                980                 985                 990

GCA GAA AGA GCC CTG GGG AGC GCT GCT GCT GAT GCA CAG AGG GCA AAG          3141
Ala Glu Arg Ala Leu Gly Ser Ala Ala Ala Asp Ala Gln Arg Ala Lys
            995                 1000                1005

AAT GGG GCC GGG GAG GCC CTG GAA ATC TCC AGT GAG ATT GAA CAG GAG          3189
Asn Gly Ala Gly Glu Ala Leu Glu Ile Ser Ser Glu Ile Glu Gln Glu
        1010                1015                1020

ATT GGG AGT CTG AAC TTG GAA GCC AAT GTG ACA GCA GAT GGA GCC TTG          3237
Ile Gly Ser Leu Asn Leu Glu Ala Asn Val Thr Ala Asp Gly Ala Leu
1025                1030                1035                1040

GCC ATG GAA AAG GGA CTG GCC TCT CTG AAG AGT GAG ATG AGG GAA GTG          3285
Ala Met Glu Lys Gly Leu Ala Ser Leu Lys Ser Glu Met Arg Glu Val
                    1045                1050                1055

GAA GGA GAG CTG GAA AGG AAG GAG CTG GAG TTT GAC ACG AAT ATG GAT          3333
Glu Gly Glu Leu Glu Arg Lys Glu Leu Glu Phe Asp Thr Asn Met Asp
                1060                1065                1070

GCA GTA CAG ATG GTG ATT ACA GAA GCC CAG AAG GTT GAT ACC AGA GCC          3381
Ala Val Gln Met Val Ile Thr Glu Ala Gln Lys Val Asp Thr Arg Ala
            1075                1080                1085

AAG AAC GCT GGG GTT ACA ATC CAA GAC ACA CTC AAC ACA TTA GAC GGC          3429
```

```
        Lys Asn Ala Gly Val Thr Ile Gln Asp Thr Leu Asn Thr Leu Asp Gly
                1090                1095                1100

CTC CTG CAT CTG ATG GAC CAG CCT CTC AGT GTA GAT GAA GAG GGG CTG       3477
Leu Leu His Leu Met Asp Gln Pro Leu Ser Val Asp Glu Glu Gly Leu
1105                1110                1115                1120

GTC TTA CTG GAG CAG AAG CTT TCC CGA GCC AAG ACC CAG ATC AAC AGC       3525
Val Leu Leu Glu Gln Lys Leu Ser Arg Ala Lys Thr Gln Ile Asn Ser
                1125                1130                1135

CAA CTG CGG CCC ATG ATG TCA GAG CTG GAA GAG AGG GCA CGT CAG CAG       3573
Gln Leu Arg Pro Met Met Ser Glu Leu Glu Glu Arg Ala Arg Gln Gln
                1140                1145                1150

AGG GGC CAC CTC CAT TTG CTG GAG ACA AGC ATA GAT GGG ATT CTG GCT       3621
Arg Gly His Leu His Leu Leu Glu Thr Ser Ile Asp Gly Ile Leu Ala
            1155                1160                1165

GAT GTG AAG AAC TTG GAG AAC ATT AGG GAC AAC CTG CCC CCA GGC TGC       3669
Asp Val Lys Asn Leu Glu Asn Ile Arg Asp Asn Leu Pro Pro Gly Cys
        1170                1175                1180

TAC AAT ACC CAG GCT CTT GAG CAA CAG TGA AGCTGCCATA AATATTTCTC         3719
Tyr Asn Thr Gln Ala Leu Glu Gln Gln  *
1185                1190

AACTGAGGTT CTTGGGATAC AGATCTCAGG GCTCGGGAGC CATGTCATGT GAGTGGGTGG     3779

GATGGGGACA TTTGAACATG TTTAATGGGT ATGCTCAGGT CAACTGACCT GACCCCATTC     3839

CTGATCCCAT GGCCAGGTGG TTGTCTTATT GCACCATACT CCTTGCTTCC TGATGCTGGG     3899

CATGAGGCAG ATAGGCACTG GTGTGAGAAT GATCAAGGAT CTGGACCCCA AGATAGACT      3959

GGATGGAAAG ACAAACTGCA CAGGCAGATG TTTGCCTCAT AATAGTCGTA AGTGGAGTCC     4019

TGGAATTTGG ACAAGTGCTG TTGGGATATA GTCAACTTAT TCTTTGAGTA ATGTGACTAA     4079

AGGAAAAAAC TTTGACTTTG CCCAGGCATG AAATTCTTCC TAATGTCAGA ACAGAGTGCA     4139

ACCCAGTCAC ACTGTGGCCA GTAAAATACT ATTGCCTCAT ATTGTCCTCT GCAAGCTTCT     4199

TGCTGATCAG AGTTCCTCCT ACTTACAACC CAGGGTGTGA ACATGTTCTC CATTTTCAAG    4259

CTGGAAGAAG TGAGCAGTGT TGGAGTGAGG ACCTGTAAGG CAGCCCATT CAGAGCTATG     4319

GTGCTTGCTG GTGCCTGCCA CCTTCAAGTT CTGGACCTGG GCATGACATC CTTTCTTTTA    4379

ATGATGCCAT GGCAACTTAG AGATTGCATT TTTATTAAAG CATTTCCTAC CAGCAAAGCA    4439

AATGTTGGGA AAGTATTTAC TTTTTCGGTT TCAAAGTGAT AGAAAAGTGT GGCTTGGGCA    4499

TTGAAAGAGG TAAAATTCTC TAGATTTATT AGTCCTAATT CAATCCTACT TTTCGAACAC    4559

CAAAAATGAT GCGCATCAAT GTATTTTATC TTATTTTCTC AATCTCCTCT CTCTTTCCTC    4619

CACCCATAAT AAGAGAATGT TCCTACTCAC ACTTCAGCTG GGTCACATCC ATCCCTCCAT    4679

TCATCCTTCC ATCCATCTTT CCATCCATTA CCTCCATCCA TCCTTCCAAC ATATATTTAT    4739

TGAGTACCTA CTGTGTGCCA GGGGCTGGTG GGACAGTGGT GACATAGTCT CTGCCCTCAT    4799

AGAGTTGATT GTCTAGTGAG GAAGACAAGC ATTTTTAAAA AATAAATTTA AACTTACAAA    4859

CTTTGTTTGT CACAAGTGGT GTTTATTGCA ATAACCGCTT GGTTTGCAAC CTCTTTGCTC    4919

AACAGAACAT ATGTTGCAAG ACCCTCCCAT GGGCACTGAG TTTGGCAAGG ATGACAGAGC    4979

TCTGGGTTGT GCACATTTCT TTGCATTCCA GCGTCACTCT GTGCCTTCTA CAACTGATTG    5039

CAACAGACTG TTGAGTTATG ATAACACCAG TGGGAATTGC TGGAGGAACC AGAGGCACTT    5099

CCACCTTGGC TGGGAAGACT ATGGTGCTGC CTTGCTTCTG TATTTCCTTG GATTTTCCTG    5159

AAAGTGTTTT TAAATAAAGA ACAATTGTTA GATGCCAAAA A                        5200

(2) INFORMATION FOR SEQ ID NO:13:
```

(i) SEQUENCE CHARACTERISTICS:
     (A) LENGTH: 1193 amino acids
     (B) TYPE: amino acid
     (D) TOPOLOGY: linear (ii) MOLECULE TYPE: protein (xi) SEQUENCE DESCRIPTION: SEQ ID NO:13:

```
Met Pro Ala Leu Trp Leu Gly Cys Cys Leu Cys Phe Ser Leu Leu Leu
 1               5                  10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
                100                 105                 110

Cys Asp Arg Cys Leu Pro Gly Phe His Met Leu Thr Asp Ala Gly Cys
            115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
                180                 185                 190

Ser Ala Ser Cys Arg Ser Ser Ala Glu Tyr Ser Val His Lys Ile Thr
            195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
                260                 265                 270

Tyr Arg Val Asp Arg Gly Gly Arg His Pro Ser Ala His Asp Val Ile
            275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
                340                 345                 350

Gly Glu Tyr Ser Thr Gly Tyr Ile Asp Asn Val Thr Leu Ile Ser Ala
            355                 360                 365
```

-continued

```
Arg Pro Val Ser Gly Ala Pro Ala Pro Trp Val Glu Gln Cys Ile Cys
    370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415

Asn Cys Gln Gly Gly Ala Cys Asp Pro Asp Thr Gly Asp Cys Tyr
                420                 425                 430

Ser Gly Asp Glu Asn Pro Asp Ile Glu Cys Ala Asp Cys Pro Ile Gly
                435                 440                 445

Phe Tyr Asn Asp Pro His Asp Pro Arg Ser Cys Lys Pro Cys Pro Cys
    450                 455                 460

His Asn Gly Phe Ser Cys Ser Val Ile Pro Glu Thr Glu Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
                500                 505                 510

Pro Cys Gln Pro Cys Gln Cys Asn Ser Asn Val Asp Pro Ser Ala Ser
    515                 520                 525

Gly Asn Cys Asp Arg Leu Thr Gly Arg Cys Leu Lys Cys Ile His Asn
    530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
    595                 600                 605

Cys Pro Ala Cys Tyr Asn Gln Val Lys Ile Gln Met Asp Gln Phe Met
    610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
                660                 665                 670

Ala Ser Arg Ser Leu Gly Leu Gln Leu Ala Lys Val Arg Ser Gln Glu
                675                 680                 685

Asn Ser Tyr Gln Ser Arg Leu Asp Asp Leu Lys Met Thr Val Glu Arg
    690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
                740                 745                 750

Gly Phe Lys Ser Leu Ala Gln Glu Ala Thr Arg Leu Ala Glu Ser His
                755                 760                 765

Val Glu Ser Ala Ser Asn Met Glu Gln Leu Thr Arg Glu Thr Glu Asp
    770                 775                 780

Tyr Ser Lys Gln Ala Leu Ser Leu Val Arg Lys Ala Leu His Glu Gly
```

-continued

```
                    785                 790                 795                 800
Val Gly Ser Gly Ser Gly Ser Pro Asp Gly Ala Val Val Gln Gly Leu
                805                 810                 815
Val Glu Lys Leu Glu Lys Thr Lys Ser Leu Ala Gln Gln Leu Thr Arg
                820                 825                 830
Glu Ala Thr Gln Ala Glu Ile Glu Ala Asp Arg Ser Tyr Gln His Ser
                835                 840                 845
Leu Arg Leu Leu Asp Ser Val Ser Pro Leu Gln Gly Val Ser Asp Gln
            850                 855                 860
Ser Phe Gln Val Glu Glu Ala Lys Arg Ile Lys Gln Lys Ala Asp Ser
865                 870                 875                 880
Leu Ser Ser Leu Val Thr Arg His Met Asp Glu Phe Lys Arg Thr Gln
                885                 890                 895
Lys Asn Leu Gly Asn Trp Lys Glu Glu Ala Gln Gln Leu Leu Gln Asn
                900                 905                 910
Gly Lys Ser Gly Arg Glu Lys Ser Asp Gln Leu Leu Ser Arg Ala Asn
            915                 920                 925
Leu Ala Lys Ser Arg Ala Gln Glu Ala Leu Ser Met Gly Asn Ala Thr
            930                 935                 940
Phe Tyr Glu Val Glu Ser Ile Leu Lys Asn Leu Arg Glu Phe Asp Leu
945                 950                 955                 960
Gln Val Asp Asn Arg Lys Ala Glu Ala Glu Ala Met Lys Arg Leu
                965                 970                 975
Ser Tyr Ile Ser Gln Lys Val Ser Asp Ala Ser Asp Lys Thr Gln Gln
                980                 985                 990
Ala Glu Arg Ala Leu Gly Ser Ala Ala Asp Ala Gln Arg Ala Lys
            995                 1000                1005
Asn Gly Ala Gly Glu Ala Leu Glu Ile Ser Ser Glu Ile Glu Gln Glu
        1010                1015                1020
Ile Gly Ser Leu Asn Leu Glu Ala Asn Val Thr Ala Asp Gly Ala Leu
1025                1030                1035                1040
Ala Met Glu Lys Gly Leu Ala Ser Leu Lys Ser Glu Met Arg Glu Val
                1045                1050                1055
Glu Gly Glu Leu Glu Arg Lys Glu Leu Glu Phe Asp Thr Asn Met Asp
                1060                1065                1070
Ala Val Gln Met Val Ile Thr Glu Ala Gln Lys Val Asp Thr Arg Ala
            1075                1080                1085
Lys Asn Ala Gly Val Thr Ile Gln Asp Thr Leu Asn Thr Leu Asp Gly
            1090                1095                1100
Leu Leu His Leu Met Asp Gln Pro Leu Ser Val Asp Glu Glu Gly Leu
1105                1110                1115                1120
Val Leu Leu Glu Gln Lys Leu Ser Arg Ala Lys Thr Gln Ile Asn Ser
                1125                1130                1135
Gln Leu Arg Pro Met Met Ser Glu Leu Glu Glu Arg Ala Arg Gln Gln
            1140                1145                1150
Arg Gly His Leu His Leu Leu Glu Thr Ser Ile Asp Gly Ile Leu Ala
            1155                1160                1165
Asp Val Lys Asn Leu Glu Asn Ile Arg Asp Asn Leu Pro Pro Gly Cys
            1170                1175                1180
Tyr Asn Thr Gln Ala Leu Glu Gln Gln
1185                1190

(2) INFORMATION FOR SEQ ID NO:14:
```

(i) SEQUENCE CHARACTERISTICS:
    (A) LENGTH: 4316 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: sig_peptide
    (B) LOCATION: 118..183

(ix) FEATURE:
    (A) NAME/KEY: CDS
    (B) LOCATION: 118..3453

(ix) FEATURE:
    (A) NAME/KEY: repeat_unit
    (B) LOCATION: 4021..4316
    (D) OTHER INFORMATION: /rpt_type= "other"
        /rpt_family= "HUMAN ALU"

(ix) FEATURE:
    (A) NAME/KEY: polyA_site
    (B) LOCATION: 4296

(xi) SEQUENCE DESCRIPTION: SEQ ID NO:14:

```
GACCACCTGA TCGAAGGAAA AGGAAGGCAC AGCGGAGCGC AGAGTGAGAA CCACCAACCG        60

AGGCGCCGGG CAGCGACCCC TGCAGCGGAG ACAGAGACTG AGCGGCCCGG CACCGCC         117

ATG CCT GCG CTC TGG CTG GGC TGC TGC CTC TGC TTC TCG CTC CTC CTG        165
Met Pro Ala Leu Trp Leu Gly Cys Cys Leu Cys Phe Ser Leu Leu Leu
1195               1200                1205                1210

CCC GCA GCC CGG GCC ACC TCC AGG AGG GAA GTC TGT GAT TGC AAT GGG        213
Pro Ala Ala Arg Ala Thr Ser Arg Arg Glu Val Cys Asp Cys Asn Gly
                1215                1220                1225

AAG TCC AGG CAG TGT ATC TTT GAT CGG GAA CTT CAC AGA CAA ACT GGT        261
Lys Ser Arg Gln Cys Ile Phe Asp Arg Glu Leu His Arg Gln Thr Gly
            1230                1235                1240

AAT GGA TTC CGC TGC CTC AAC TGC AAT GAC AAC ACT GAT GGC ATT CAC        309
Asn Gly Phe Arg Cys Leu Asn Cys Asn Asp Asn Thr Asp Gly Ile His
        1245                1250                1255

TGC GAG AAG TGC AAG AAT GGC TTT TAC CGG CAC AGA GAA AGG GAC CGC        357
Cys Glu Lys Cys Lys Asn Gly Phe Tyr Arg His Arg Glu Arg Asp Arg
    1260                1265                1270

TGT TTG CCC TGC AAT TGT AAC TCC AAA GGT TCT CTT AGT GCT CGA TGT        405
Cys Leu Pro Cys Asn Cys Asn Ser Lys Gly Ser Leu Ser Ala Arg Cys
1275                1280                1285                1290

GAC AAC TCT GGA CGG TGC AGC TGT AAA CCA GGT GTG ACA GGA GCC AGA        453
Asp Asn Ser Gly Arg Cys Ser Cys Lys Pro Gly Val Thr Gly Ala Arg
                1295                1300                1305

TGC GAC CGA TGT CTG CCA GGC TTC CAC ATG CTC ACG GAT GCG GGG TGC        501
Cys Asp Arg Cys Leu Pro Gly Phe His Met Leu Thr Asp Ala Gly Cys
            1310                1315                1320

ACC CAA GAC CAG AGA CTG CTA GAC TCC AAG TGT GAC TGT GAC CCA GCT        549
Thr Gln Asp Gln Arg Leu Leu Asp Ser Lys Cys Asp Cys Asp Pro Ala
        1325                1330                1335

GGC ATC GCA GGG CCC TGT GAC GCG GGC CGC TGT GTC TGC AAG CCA GCT        597
Gly Ile Ala Gly Pro Cys Asp Ala Gly Arg Cys Val Cys Lys Pro Ala
    1340                1345                1350

GTT ACT GGA GAA CGC TGT GAT AGG TGT CGA TCA GGT TAC TAT AAT CTG        645
Val Thr Gly Glu Arg Cys Asp Arg Cys Arg Ser Gly Tyr Tyr Asn Leu
1355                1360                1365                1370

GAT GGG GGG AAC CCT GAG GGC TGT ACC CAG TGT TTC TGC TAT GGG CAT        693
Asp Gly Gly Asn Pro Glu Gly Cys Thr Gln Cys Phe Cys Tyr Gly His
```

-continued

|  |  |
|---|---|
| `TCA GCC AGC TGC CGC AGC TCT GCA GAA TAC AGT GTC CAT AAG ATC ACC`<br>`Ser Ala Ser Cys Arg Ser Ser Ala Glu Tyr Ser Val His Lys Ile Thr`<br>`         1390              1395              1400` | 741 |
| `TCT ACC TTT CAT CAA GAT GTT GAT GGC TGG AAG GCT GTC CAA CGA AAT`<br>`Ser Thr Phe His Gln Asp Val Asp Gly Trp Lys Ala Val Gln Arg Asn`<br>`    1405              1410              1415` | 789 |
| `GGG TCT CCT GCA AAG CTC CAA TGG TCA CAG CGC CAT CAA GAT GTG TTT`<br>`Gly Ser Pro Ala Lys Leu Gln Trp Ser Gln Arg His Gln Asp Val Phe`<br>`1420              1425              1430` | 837 |
| `AGC TCA GCC CAA CGA CTA GAT CCT GTC TAT TTT GTG GCT CCT GCC AAA`<br>`Ser Ser Ala Gln Arg Leu Asp Pro Val Tyr Phe Val Ala Pro Ala Lys`<br>`1435              1440              1445              1450` | 885 |
| `TTT CTT GGG AAT CAA CAG GTG AGC TAT GGG CAA AGC CTG TCC TTT GAC`<br>`Phe Leu Gly Asn Gln Gln Val Ser Tyr Gly Gln Ser Leu Ser Phe Asp`<br>`         1455              1460              1465` | 933 |
| `TAC CGT GTG GAC AGA GGA GGC AGA CAC CCA TCT GCC CAT GAT GTG ATC`<br>`Tyr Arg Val Asp Arg Gly Gly Arg His Pro Ser Ala His Asp Val Ile`<br>`    1470              1475              1480` | 981 |
| `CTG GAA GGT GCT GGT CTA CGG ATC ACA GCT CCC TTG ATG CCA CTT GGC`<br>`Leu Glu Gly Ala Gly Leu Arg Ile Thr Ala Pro Leu Met Pro Leu Gly`<br>`1485              1490              1495` | 1029 |
| `AAG ACA CTG CCT TGT GGG CTC ACC AAG ACT TAC ACA TTC AGG TTA AAT`<br>`Lys Thr Leu Pro Cys Gly Leu Thr Lys Thr Tyr Thr Phe Arg Leu Asn`<br>`1500              1505              1510` | 1077 |
| `GAG CAT CCA AGC AAT AAT TGG AGC CCC CAG CTG AGT TAC TTT GAG TAT`<br>`Glu His Pro Ser Asn Asn Trp Ser Pro Gln Leu Ser Tyr Phe Glu Tyr`<br>`1515              1520              1525              1530` | 1125 |
| `CGA AGG TTA CTG CGG AAT CTC ACA GCC CTC CGC ATC CGA GCT ACA TAT`<br>`Arg Arg Leu Leu Arg Asn Leu Thr Ala Leu Arg Ile Arg Ala Thr Tyr`<br>`         1535              1540              1545` | 1173 |
| `GGA GAA TAC AGT ACT GGG TAC ATT GAC AAT GTG ACC CTG ATT TCA GCC`<br>`Gly Glu Tyr Ser Thr Gly Tyr Ile Asp Asn Val Thr Leu Ile Ser Ala`<br>`    1550              1555              1560` | 1221 |
| `CGC CCT GTC TCT GGA GCC CCA GCA CCC TGG GTT GAA CAG TGT ATA TGT`<br>`Arg Pro Val Ser Gly Ala Pro Ala Pro Trp Val Glu Gln Cys Ile Cys`<br>`         1565              1570              1575` | 1269 |
| `CCT GTT GGG TAC AAG GGG CAA TTC TGC CAG GAT TGT GCT TCT GGC TAC`<br>`Pro Val Gly Tyr Lys Gly Gln Phe Cys Gln Asp Cys Ala Ser Gly Tyr`<br>`    1580              1585              1590` | 1317 |
| `AAG AGA GAT TCA GCG AGA CTG GGG CCT TTT GGC ACC TGT ATT CCT TGT`<br>`Lys Arg Asp Ser Ala Arg Leu Gly Pro Phe Gly Thr Cys Ile Pro Cys`<br>`1595              1600              1605              1610` | 1365 |
| `AAC TGT CAA GGG GGA GGG GCC TGT GAT CCA GAC ACA GGA GAT TGT TAT`<br>`Asn Cys Gln Gly Gly Gly Ala Cys Asp Pro Asp Thr Gly Asp Cys Tyr`<br>`         1615              1620              1625` | 1413 |
| `TCA GGG GAT GAG AAT CCT GAC ATT GAG TGT GCT GAC TGC CCA ATT GGT`<br>`Ser Gly Asp Glu Asn Pro Asp Ile Glu Cys Ala Asp Cys Pro Ile Gly`<br>`    1630              1635              1640` | 1461 |
| `TTC TAC AAC GAT CCG CAC GAC CCC CGC AGC TGC AAG CCA TGT CCC TGT`<br>`Phe Tyr Asn Asp Pro His Asp Pro Arg Ser Cys Lys Pro Cys Pro Cys`<br>`         1645              1650              1655` | 1509 |
| `CAT AAC GGG TTC AGC TGC TCA GTG ATT CCG GAG ACG GAG GAG GTG GTG`<br>`His Asn Gly Phe Ser Cys Ser Val Ile Pro Glu Thr Glu Glu Val Val`<br>`    1660              1665              1670` | 1557 |
| `TGC AAT AAC TGC CCT CCC GGG GTC ACC GGT GCC CGC TGT GAG CTC TGT`<br>`Cys Asn Asn Cys Pro Pro Gly Val Thr Gly Ala Arg Cys Glu Leu Cys`<br>`1675              1680              1685              1690` | 1605 |
| `GCT GAT GGC TAC TTT GGG GAC CCC TTT GGT GAA CAT GGC CCA GTG AGG` | 1653 |

-continued

```
                Ala Asp Gly Tyr Phe Gly Asp Pro Phe Gly Glu His Gly Pro Val Arg
                                1695                1700                1705

CCT TGT CAG CCC TGT CAA TGC AAC AGC AAT GTG GAC CCC AGT GCC TCT            1701
Pro Cys Gln Pro Cys Gln Cys Asn Ser Asn Val Asp Pro Ser Ala Ser
            1710                1715                1720

GGG AAT TGT GAC CGG CTG ACA GGC AGG TGT TTG AAG TGT ATC CAC AAC            1749
Gly Asn Cys Asp Arg Leu Thr Gly Arg Cys Leu Lys Cys Ile His Asn
        1725                1730                1735

ACA GCC GGC ATC TAC TGC GAC CAG TGC AAA GCA GGC TAC TTC GGG GAC            1797
Thr Ala Gly Ile Tyr Cys Asp Gln Cys Lys Ala Gly Tyr Phe Gly Asp
    1740                1745                1750

CCA TTG GCT CCC AAC CCA GCA GAC AAG TGT CGA GCT TGC AAC TGT AAC            1845
Pro Leu Ala Pro Asn Pro Ala Asp Lys Cys Arg Ala Cys Asn Cys Asn
1755                1760                1765                1770

CCC ATG GGC TCA GAG CCT GTA GGA TGT CGA AGT GAT GGC ACC TGT GTT            1893
Pro Met Gly Ser Glu Pro Val Gly Cys Arg Ser Asp Gly Thr Cys Val
                1775                1780                1785

TGC AAG CCA GGA TTT GGT GGC CCC AAC TGT GAG CAT GGA GCA TTC AGC            1941
Cys Lys Pro Gly Phe Gly Gly Pro Asn Cys Glu His Gly Ala Phe Ser
            1790                1795                1800

TGT CCA GCT TGC TAT AAT CAA GTG AAG ATT CAG ATG GAT CAG TTT ATG            1989
Cys Pro Ala Cys Tyr Asn Gln Val Lys Ile Gln Met Asp Gln Phe Met
        1805                1810                1815

CAG CAG CTT CAG AGA ATG GAG GCC CTG ATT TCA AAG GCT CAG GGT GGT            2037
Gln Gln Leu Gln Arg Met Glu Ala Leu Ile Ser Lys Ala Gln Gly Gly
    1820                1825                1830

GAT GGA GTA GTA CCT GAT ACA GAG CTG GAA GGC AGG ATG CAG CAG GCT            2085
Asp Gly Val Val Pro Asp Thr Glu Leu Glu Gly Arg Met Gln Gln Ala
1835                1840                1845                1850

GAG CAG GCC CTT CAG GAC ATT CTG AGA GAT GCC CAG ATT TCA GAA GGT            2133
Glu Gln Ala Leu Gln Asp Ile Leu Arg Asp Ala Gln Ile Ser Glu Gly
                1855                1860                1865

GCT AGC AGA TCC CTT GGT CTC CAG TTG GCC AAG GTG AGG AGC CAA GAG            2181
Ala Ser Arg Ser Leu Gly Leu Gln Leu Ala Lys Val Arg Ser Gln Glu
            1870                1875                1880

AAC AGC TAC CAG AGC CGC CTG GAT GAC CTC AAG ATG ACT GTG GAA AGA            2229
Asn Ser Tyr Gln Ser Arg Leu Asp Asp Leu Lys Met Thr Val Glu Arg
        1885                1890                1895

GTT CGG GCT CTG GGA AGT CAG TAC CAG AAC CGA GTT CGG GAT ACT CAC            2277
Val Arg Ala Leu Gly Ser Gln Tyr Gln Asn Arg Val Arg Asp Thr His
    1900                1905                1910

AGG CTC ATC ACT CAG ATG CAG CTG AGC CTG GCA GAA AGT GAA GCT TCC            2325
Arg Leu Ile Thr Gln Met Gln Leu Ser Leu Ala Glu Ser Glu Ala Ser
1915                1920                1925                1930

TTG GGA AAC ACT AAC ATT CCT GCC TCA GAC CAC TAC GTG GGG CCA AAT            2373
Leu Gly Asn Thr Asn Ile Pro Ala Ser Asp His Tyr Val Gly Pro Asn
                1935                1940                1945

GGC TTT AAA AGT CTG GCT CAG GAG GCC ACA AGA TTA GCA GAA AGC CAC            2421
Gly Phe Lys Ser Leu Ala Gln Glu Ala Thr Arg Leu Ala Glu Ser His
            1950                1955                1960

GTT GAG TCA GCC AGT AAC ATG GAG CAA CTG ACA AGG GAA ACT GAG GAC            2469
Val Glu Ser Ala Ser Asn Met Glu Gln Leu Thr Arg Glu Thr Glu Asp
        1965                1970                1975

TAT TCC AAA CAA GCC CTC TCA CTG GTG CGC AAG GCC CTG CAT GAA GGA            2517
Tyr Ser Lys Gln Ala Leu Ser Leu Val Arg Lys Ala Leu His Glu Gly
    1980                1985                1990

GTC GGA AGC GGA AGC GGT AGC CCG GAC GGT GCT GTG GTG CAA GGG CTT            2565
Val Gly Ser Gly Ser Gly Ser Pro Asp Gly Ala Val Val Gln Gly Leu
1995                2000                2005                2010
```

-continued

```
GTG GAA AAA TTG GAG AAA ACC AAG TCC CTG GCC CAG CAG TTG ACA AGG      2613
Val Glu Lys Leu Glu Lys Thr Lys Ser Leu Ala Gln Gln Leu Thr Arg
            2015                2020                2025

GAG GCC ACT CAA GCG GAA ATT GAA GCA GAT AGG TCT TAT CAG CAC AGT      2661
Glu Ala Thr Gln Ala Glu Ile Glu Ala Asp Arg Ser Tyr Gln His Ser
            2030                2035                2040

CTC CGC CTC CTG GAT TCA GTG TCT CCG CTT CAG GGA GTC AGT GAT CAG      2709
Leu Arg Leu Leu Asp Ser Val Ser Pro Leu Gln Gly Val Ser Asp Gln
            2045                2050                2055

TCC TTT CAG GTG GAA GAA GCA AAG AGG ATC AAA CAA AAA GCG GAT TCA      2757
Ser Phe Gln Val Glu Glu Ala Lys Arg Ile Lys Gln Lys Ala Asp Ser
            2060                2065                2070

CTC TCA AGC CTG GTA ACC AGG CAT ATG GAT GAG TTC AAG CGT ACA CAA      2805
Leu Ser Ser Leu Val Thr Arg His Met Asp Glu Phe Lys Arg Thr Gln
2075                2080                2085                2090

AAG AAT CTG GGA AAC TGG AAA GAA GAA GCA CAG CAG CTC TTA CAG AAT      2853
Lys Asn Leu Gly Asn Trp Lys Glu Glu Ala Gln Gln Leu Leu Gln Asn
            2095                2100                2105

GGA AAA AGT GGG AGA GAG AAA TCA GAT CAG CTG CTT TCC CGT GCC AAT      2901
Gly Lys Ser Gly Arg Glu Lys Ser Asp Gln Leu Leu Ser Arg Ala Asn
            2110                2115                2120

CTT GCT AAA AGC AGA GCA CAA GAA GCA CTG AGT ATG GGC AAT GCC ACT      2949
Leu Ala Lys Ser Arg Ala Gln Glu Ala Leu Ser Met Gly Asn Ala Thr
            2125                2130                2135

TTT TAT GAA GTT GAG AGC ATC CTT AAA AAC CTC AGA GAG TTT GAC CTG      2997
Phe Tyr Glu Val Glu Ser Ile Leu Lys Asn Leu Arg Glu Phe Asp Leu
            2140                2145                2150

CAG GTG GAC AAC AGA AAA GCA GAA GCT GAA GAA GCC ATG AAG AGA CTC      3045
Gln Val Asp Asn Arg Lys Ala Glu Ala Glu Glu Ala Met Lys Arg Leu
2155                2160                2165                2170

TCC TAC ATC AGC CAG AAG GTT TCA GAT GCC AGT GAC AAG ACC CAG CAA      3093
Ser Tyr Ile Ser Gln Lys Val Ser Asp Ala Ser Asp Lys Thr Gln Gln
            2175                2180                2185

GCA GAA AGA GCC CTG GGG AGC GCT GCT GCT GAT GCA CAG AGG GCA AAG      3141
Ala Glu Arg Ala Leu Gly Ser Ala Ala Ala Asp Ala Gln Arg Ala Lys
            2190                2195                2200

AAT GGG GCC GGG GAG GCC CTG GAA ATC TCC AGT GAG ATT GAA CAG GAG      3189
Asn Gly Ala Gly Glu Ala Leu Glu Ile Ser Ser Glu Ile Glu Gln Glu
            2205                2210                2215

ATT GGG AGT CTG AAC TTG GAA GCC AAT GTG ACA GCA GAT GGA GCC TTG      3237
Ile Gly Ser Leu Asn Leu Glu Ala Asn Val Thr Ala Asp Gly Ala Leu
            2220                2225                2230

GCC ATG GAA AAG GGA CTG GCC TCT CTG AAG AGT GAG ATG AGG GAA GTG      3285
Ala Met Glu Lys Gly Leu Ala Ser Leu Lys Ser Glu Met Arg Glu Val
2235                2240                2245                2250

GAA GGA GAG CTG GAA AGG AAG GAG CTG GAG TTT GAC ACG AAT ATG GAT      3333
Glu Gly Glu Leu Glu Arg Lys Glu Leu Glu Phe Asp Thr Asn Met Asp
            2255                2260                2265

GCA GTA CAG ATG GTG ATT ACA GAA GCC CAG AAG GTT GAT ACC AGA GCC      3381
Ala Val Gln Met Val Ile Thr Glu Ala Gln Lys Val Asp Thr Arg Ala
            2270                2275                2280

AAG AAC GCT GGG GTT ACA ATC CAA GAC ACA CTC AAC ACA TTA GAC GGC      3429
Lys Asn Ala Gly Val Thr Ile Gln Asp Thr Leu Asn Thr Leu Asp Gly
            2285                2290                2295

CTC CTG CAT CTG ATG GGT ATG TGA ACCCACAACC CACAACCTTC CAGCTCCATG     3483
Leu Leu His Leu Met Gly Met  *
    2300                2305

CTCCAGGGCT TGCTCCAGA ACACTCACTA TACCTAGCCC CAGCAAAGGG GAGTCTCAGC     3543

TTTCCTTAAG GATATCAGTA AATGTGCTTT GTTTCCAGGC CCAGATAACT TTCGGCAGGT    3603
```

```
TCCCCTTACAT TTACTGGACC CTGTTTTACC GTTGCTAAGA TGGGTCACTG AACACCTATT    3663

GCACTTGGGG GTAAAGGTCT GTGGGCCAAA GAACAGGTGT ATATAAGCAA CTTCACAGAA    3723

CACGAGACAG CTTGGGAATC CTGCTAAAGA GTCTGGCCTG GACCCTGAGA AGCCAGTGGA    3783

CAGTTTTAAG CAGAGGAATA ACATCACCAC TGTATATTTC AGAAAGATCA CTAGGGCAGC    3843

CGAGTGGAGG AAAGCTTGAA GAGGGGGTTA GAGAGAAGGC AGGTTGAGAC TACTTAAGAT    3903

ATTGTTGAAA TAATTGAAGA GAGAAATGAC AGGAGCCTGC TCTAAGGCAG TAGAATGGTG    3963

GCTGGGAAGA TGTGAAGGAA GATTTTCCCA GTCTGTGAAG TCAAGAATCA CTTGCCGGCC    4023

GGGTGTGGTG GCTCACGCCT GTAATTCTAG CACTTTGGGA GACTGAAGCG GGTGGATCAC    4083

CCGAGGTCAG GAGTTGAAGA CCAGCCTGGC CAACATGGTG AAACCCTGTC TCTACTAAAA    4143

GTACAAAAAT TAGCTGGATG ATGGTGGTGG GCGCCTGTAA TTCCAGCTAC TCAGGAGTCT    4203

GAGGCAGGAG AATCGCTTGA ACCCAGGAGG CGAGGTTACA GTGAGCCAAG ATTGCACCAC    4263

TGCTCTTCCA GCCTGGGAAC AGAGAGACTG CCTAAAAAAA AAAAAAAAA AAA            4316
```

(2) INFORMATION FOR SEQ ID NO:15:

(i) SEQUENCE CHARACTERISTICS:
        (A) LENGTH: 1111 amino acids
        (B) TYPE: amino acid
        (D) TOPOLOGY: linear (ii) MOLECULE TYPE: protein (xi) SEQUENCE DESCRIPTION: SEQ ID NO:15:

```
Met Pro Ala Leu Trp Leu Gly Cys Cys Leu Cys Phe Ser Leu Leu Leu
 1               5                  10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220
```

-continued

```
Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
            245                 250                 255

Phe Leu Gly Asn Gln Gln Val Ser Tyr Gly Gln Ser Leu Ser Phe Asp
                260                 265                 270

Tyr Arg Val Asp Arg Gly Gly Arg His Pro Ser Ala His Asp Val Ile
            275                 280                 285

Leu Glu Gly Ala Gly Leu Arg Ile Thr Ala Pro Leu Met Pro Leu Gly
        290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365

Arg Pro Val Ser Gly Ala Pro Ala Pro Trp Val Glu Gln Cys Ile Cys
370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
            405                 410                 415

Asn Cys Gln Gly Gly Ala Cys Asp Pro Asp Thr Gly Asp Cys Tyr
                420                 425                 430

Ser Gly Asp Glu Asn Pro Asp Ile Glu Cys Ala Asp Cys Pro Ile Gly
            435                 440                 445

Phe Tyr Asn Asp Pro His Asp Pro Arg Ser Cys Lys Pro Cys Pro Cys
        450                 455                 460

His Asn Gly Phe Ser Cys Ser Val Ile Pro Glu Thr Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
            500                 505                 510

Pro Cys Gln Pro Cys Gln Cys Asn Ser Asn Val Asp Pro Ser Ala Ser
        515                 520                 525

Gly Asn Cys Asp Arg Leu Thr Gly Arg Cys Leu Lys Cys Ile His Asn
530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
            565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
            595                 600                 605

Cys Pro Ala Cys Tyr Asn Gln Val Lys Ile Gln Met Asp Gln Phe Met
        610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
```

-continued

```
                645                 650                 655
Glu Gln Ala Leu Gln Asp Ile Leu Arg Asp Ala Gln Ile Ser Glu Gly
                660                 665                 670
Ala Ser Arg Ser Leu Gly Leu Gln Leu Ala Lys Val Arg Ser Gln Glu
                675                 680                 685
Asn Ser Tyr Gln Ser Arg Leu Asp Asp Leu Lys Met Thr Val Glu Arg
                690                 695                 700
Val Arg Ala Leu Gly Ser Gln Tyr Gln Asn Arg Val Arg Asp Thr His
705                 710                 715                 720
Arg Leu Ile Thr Gln Met Gln Leu Ser Leu Ala Glu Ser Glu Ala Ser
                725                 730                 735
Leu Gly Asn Thr Asn Ile Pro Ala Ser Asp His Tyr Val Gly Pro Asn
                740                 745                 750
Gly Phe Lys Ser Leu Ala Gln Glu Ala Thr Arg Leu Ala Glu Ser His
                755                 760                 765
Val Glu Ser Ala Ser Asn Met Glu Gln Leu Thr Arg Glu Thr Glu Asp
                770                 775                 780
Tyr Ser Lys Gln Ala Leu Ser Leu Val Arg Lys Ala Leu His Glu Gly
785                 790                 795                 800
Val Gly Ser Gly Ser Gly Ser Pro Asp Gly Ala Val Val Gln Gly Leu
                805                 810                 815
Val Glu Lys Leu Glu Lys Thr Lys Ser Leu Ala Gln Gln Leu Thr Arg
                820                 825                 830
Glu Ala Thr Gln Ala Glu Ile Glu Ala Asp Arg Ser Tyr Gln His Ser
                835                 840                 845
Leu Arg Leu Leu Asp Ser Val Ser Pro Leu Gln Gly Val Ser Asp Gln
                850                 855                 860
Ser Phe Gln Val Glu Glu Ala Lys Arg Ile Lys Gln Lys Ala Asp Ser
865                 870                 875                 880
Leu Ser Ser Leu Val Thr Arg His Met Asp Glu Phe Lys Arg Thr Gln
                885                 890                 895
Lys Asn Leu Gly Asn Trp Lys Glu Glu Ala Gln Gln Leu Leu Gln Asn
                900                 905                 910
Gly Lys Ser Gly Arg Glu Lys Ser Asp Gln Leu Leu Ser Arg Ala Asn
                915                 920                 925
Leu Ala Lys Ser Arg Ala Gln Glu Ala Leu Ser Met Gly Asn Ala Thr
                930                 935                 940
Phe Tyr Glu Val Glu Ser Ile Leu Lys Asn Leu Arg Glu Phe Asp Leu
945                 950                 955                 960
Gln Val Asp Asn Arg Lys Ala Glu Ala Glu Ala Met Lys Arg Leu
                965                 970                 975
Ser Tyr Ile Ser Gln Lys Val Ser Asp Ala Ser Asp Lys Thr Gln Gln
                980                 985                 990
Ala Glu Arg Ala Leu Gly Ser Ala Ala Asp Ala Gln Arg Ala Lys
                995                 1000                1005
Asn Gly Ala Gly Glu Ala Leu Glu Ile Ser Ser Glu Ile Glu Gln Glu
                1010                1015                1020
Ile Gly Ser Leu Asn Leu Glu Ala Asn Val Thr Ala Asp Gly Ala Leu
1025                1030                1035                1040
Ala Met Glu Lys Gly Leu Ala Ser Leu Lys Ser Glu Met Arg Glu Val
                1045                1050                1055
Glu Gly Glu Leu Glu Arg Lys Glu Leu Glu Phe Asp Thr Asn Met Asp
                1060                1065                1070
```

```
Ala Val Gln Met Val Ile Thr Glu Ala Gln Lys Val Asp Thr Arg Ala
        1075                1080                1085

Lys Asn Ala Gly Val Thr Ile Gln Asp Thr Leu Asn Thr Leu Asp Gly
        1090                1095                1100

Leu Leu His Leu Met Gly Met
1105                1110
```

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligomer primers"

(xi) SEQUENCE DESCRIPTION: SEQ ID NO:16:

GAGCGCAGAG TGAGAACCAC                            20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligomer primers"

(xi) SEQUENCE DESCRIPTION: SEQ ID NO:17:

ACTGTATTCT GCAGAGCTGC                            20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligomer primers"

(xi) SEQUENCE DESCRIPTION: SEQ ID NO:18:

TTCCTTTCCCCTACCTTGTG                            20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO:19:

TGTGGAAGCCTGGCAGACAT                            20